US007247269B2

(12) United States Patent
Keidar

(10) Patent No.: US 7,247,269 B2
(45) Date of Patent: Jul. 24, 2007

(54) METHOD FOR MAKING A SPIRAL ARRAY ULTRASOUND TRANSDUCER

(75) Inventor: Yaron Keidar, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 122 days.

(21) Appl. No.: 10/623,894

(22) Filed: Jul. 21, 2003

(65) Prior Publication Data

US 2005/0015953 A1 Jan. 27, 2005

(51) Int. Cl.
*B28B 11/08* (2006.01)
*H04R 17/00* (2006.01)
(52) U.S. Cl. ........................... 264/678; 264/519
(58) Field of Classification Search ............... 264/435
See application file for complete search history.

(56) References Cited

U.S. PATENT DOCUMENTS

| 4,135,109 | A | * | 1/1979 | Gingerich et al. ........... 310/369 |
|---|---|---|---|---|
| 4,449,528 | A | | 5/1984 | Auth et al. |
| 4,522,205 | A | | 6/1985 | Taylor et al. |
| 4,569,801 | A | | 2/1986 | Molloy et al. |
| 4,641,649 | A | | 2/1987 | Walinsky et al. |
| 4,662,368 | A | | 5/1987 | Hussein et al. |
| 4,672,962 | A | | 6/1987 | Hershenson |
| 4,673,563 | A | | 6/1987 | Berne et al. |
| 4,676,258 | A | | 6/1987 | Inokuchi et al. |
| 4,790,311 | A | | 12/1988 | Ruiz |
| 4,807,620 | A | | 2/1989 | Strul et al. |
| 4,898,591 | A | | 2/1990 | Jang et al. |
| 4,938,217 | A | | 7/1990 | Lee |
| 4,998,933 | A | | 3/1991 | Eggers et al. |
| 5,035,694 | A | | 7/1991 | Kasprzyk et al. |
| 5,078,736 | A | | 1/1992 | Behl |
| 5,104,393 | A | | 4/1992 | Isner et al. |
| 5,178,618 | A | | 1/1993 | Kandarpa |
| 5,190,540 | A | | 3/1993 | Lee |
| 5,226,430 | A | | 7/1993 | Spears et al. |
| 5,292,321 | A | | 3/1994 | Lee |
| 5,295,484 | A | | 3/1994 | Marcus |

(Continued)

FOREIGN PATENT DOCUMENTS

DE 198114697 C1 10/1999

(Continued)

OTHER PUBLICATIONS

English Abstract JP06120062A.*

(Continued)

*Primary Examiner*—Carlos Lopez
(74) *Attorney, Agent, or Firm*—Vincent J. Serrao

(57) ABSTRACT

The present invention relates to a method for making an ablation transducer having a plurality of helical elements that can be operated out of phase to orient the acoustical energy beam forward or backward in the longitudinal direction. The transducers includes a cylindrical inner electrode, a cylindrical piezoelectric material disposed over the inner electrode, and a cylindrical outer electrode disposed over the cylindrical piezoelectric material. Spiral grooves are cut through at least the outer electrode separating the transducer into a plurality of functionally discrete helical transducer segments. The helical transducer segments can be operated independent from one another. An array of intertwined helical transducers arranged linearly along a helical axis are also contemplated.

18 Claims, 13 Drawing Sheets

U.S. PATENT DOCUMENTS

| | | | |
|---|---|---|---|
| 5,348,554 A | 9/1994 | Imran et al. | |
| 5,423,811 A | 6/1995 | Imran et al. | |
| 5,427,119 A | 6/1995 | Swartz et al. | |
| 5,449,380 A | 9/1995 | Chin | |
| 5,487,385 A | 1/1996 | Avitall | |
| 5,497,119 A | 3/1996 | Tedrow et al. | |
| 5,505,730 A | 4/1996 | Edwards | |
| 5,545,161 A | 8/1996 | Imran | |
| 5,545,193 A | 8/1996 | Fleischmann et al. | |
| 5,549,661 A | 8/1996 | Kordis et al. | |
| 5,558,672 A | 9/1996 | Edwards et al. | |
| 5,562,720 A | 10/1996 | Stern et al. | |
| 5,564,440 A | 10/1996 | Swartz et al. | |
| 5,569,241 A | 10/1996 | Edwards | |
| 5,575,766 A | 11/1996 | Swartz et al. | |
| 5,575,788 A | 11/1996 | Baker et al. | |
| 5,575,810 A | 11/1996 | Swanson et al. | |
| 5,582,609 A | 12/1996 | Swanson et al. | |
| 5,590,657 A | 1/1997 | Cain et al. | |
| 5,617,854 A | 4/1997 | Munsif | |
| 5,658,278 A | 8/1997 | Imran et al. | |
| 5,687,723 A | 11/1997 | Avitall | |
| 5,688,267 A | 11/1997 | Panescu et al. | |
| 5,697,927 A | 12/1997 | Imran et al. | |
| 5,702,438 A | 12/1997 | Avitall | |
| 5,722,403 A | 3/1998 | McGee et al. | |
| 5,769,846 A | 6/1998 | Edwards et al. | |
| 5,855,049 A * | 1/1999 | Corbett et al. | 29/25.35 |
| 5,938,660 A | 8/1999 | Swartz et al. | |
| 5,971,983 A | 10/1999 | Lesh | |
| 6,012,457 A | 1/2000 | Lesh | |
| 6,024,740 A | 2/2000 | Lesh et al. | |
| 6,117,101 A | 9/2000 | Diederich et al. | |
| 2002/0059708 A1* | 5/2002 | Zhang et al. | 29/25.35 |
| 2002/0136969 A1* | 9/2002 | Hiller et al. | 430/18 |

FOREIGN PATENT DOCUMENTS

| | | |
|---|---|---|
| JP | 06120062 A * | 4/1994 |
| JP | 4061200062 A | 4/1994 |
| WO | WO 93/20767 A1 | 10/1993 |
| WO | WO 94/21165 A1 | 9/1994 |
| WO | WO 96/10961 A1 | 4/1996 |
| WO | WO 96/26675 A1 | 9/1996 |
| WO | WO 96/32897 A1 | 10/1996 |
| WO | WO 97/32525 A1 | 9/1997 |
| WO | WO 97/37607 A2 | 10/1997 |
| WO | WO 98/02201 A1 | 1/1998 |
| WO | WO 99/00064 A1 | 1/1999 |
| WO | WO 99/02096 A1 | 1/1999 |
| WO | WO 01/68173 A3 | 9/2001 |

OTHER PUBLICATIONS

Koshal et al., Manufacturering Engineer's Reference Book, copyright 1993, Butterworth-Heinemann, pp. 14/19, 14/20, 14/28, 14/34, 14/35.*

Licari, Coating Materials for Electronic Applications Polymers, Processes, Reliability, Testing, copyright 2003, pp. 226-229.*

International Search Report dated Jul. 20, 2005 for corresponding Appl. No. PCT/US04/23332.

"Percutaneous Laser Balloon Coagulation of Accessory Pathways" by Linda P. McMath, et al., Proceedings of Diagnostic and Therapeutic Cardiovascular Interventions, pp. 165-171, Jan. 20-22, 1991.

"Long-term Effects of Percutaneous Laser Balloon Ablation from the Canine Coronary Sinus", by Claudio D. Schuger, MD, et al.; Circulation vol. 86, No. 3, Sep., 1992, pp. 947-954.

"Induction of Hyperthermia Using an Intracavitary Multielement Ultrasonic Applicator", by Chris I. Diederich and Kullervo Hynynen; Transactions on Biomedical Engineering, vol. 36, No. 4, pp. 432-438, Apr. 1989.

"A Focal Source of Atrial Fibrillation Treated by Discrete Radiofrequency Ablation", Pierre Jais, MD, et al., Circulation Vo. 95, No. 3, Feb. 4, 1997, pp. 572-576.

"The Development of Intracavitary Ultrasonic Applicators for Hyperthermia: A Design and Experimental Study" C.J. Diederich et al., Medical Physics, vol. 17, No. 4, pp. 626-634 Jul./Aug. 1990.

NASPE 17th Annual Scientific Sessions Abstract Form, Biatrial Dimensions Relevant to Catheter Ablation Pierre Jais, MD, et al., Dec. 1, 1995.

"Right and Left Atrial Radiofrequency Catheter Therapy of Paroxysmal Atrial Fibrillation" Michel Haissaguerre, MD, et al., Journal of Cardiovascular Electrophysiology, vol. 7, No. 12, pp. 1133-1144, Dec. 1996.

"Nonpharmacologic Management, Catheter Ablation" Gerhard Hindricks, MD, et al., Current Management of Arrhythmias, pp. 373-378, 1991.

"The Surgical Treatment of Atrial Fibrillation. I. Summary" Cox, J.L. et al., Thoracic and Cardiovascular Surgery 101(3), pp. 402-405 (1991).

"The Surgical Treatment of Atrial Fibrillation. Cox, J.L., et al., IV Surgical Technique", Thoracic and Cardiovascular Surgery 101(4), pp. 584-592 (1991).

"Simple Left Atrial Procedure for Chronic Atrial Fibrillation Associated with Mitral Valve Disease" Sueda et al. 1996.

"Feasibility of RF Powered Thermal Balloon Ablation of Atrioventricular Bypass Tracts via the Coronary Sinus: In vivo Canine Studies," PACE Fram et al., vol. 18, p. 1518-1530 (1995).

"Laser Machining of High Density Two-Dimensional Ultrasound Arrays", Corbett et al., MicroSound Systems, Inc, 349*25 SE Douglass Street, Snoqualmic, WA 98065.

* cited by examiner

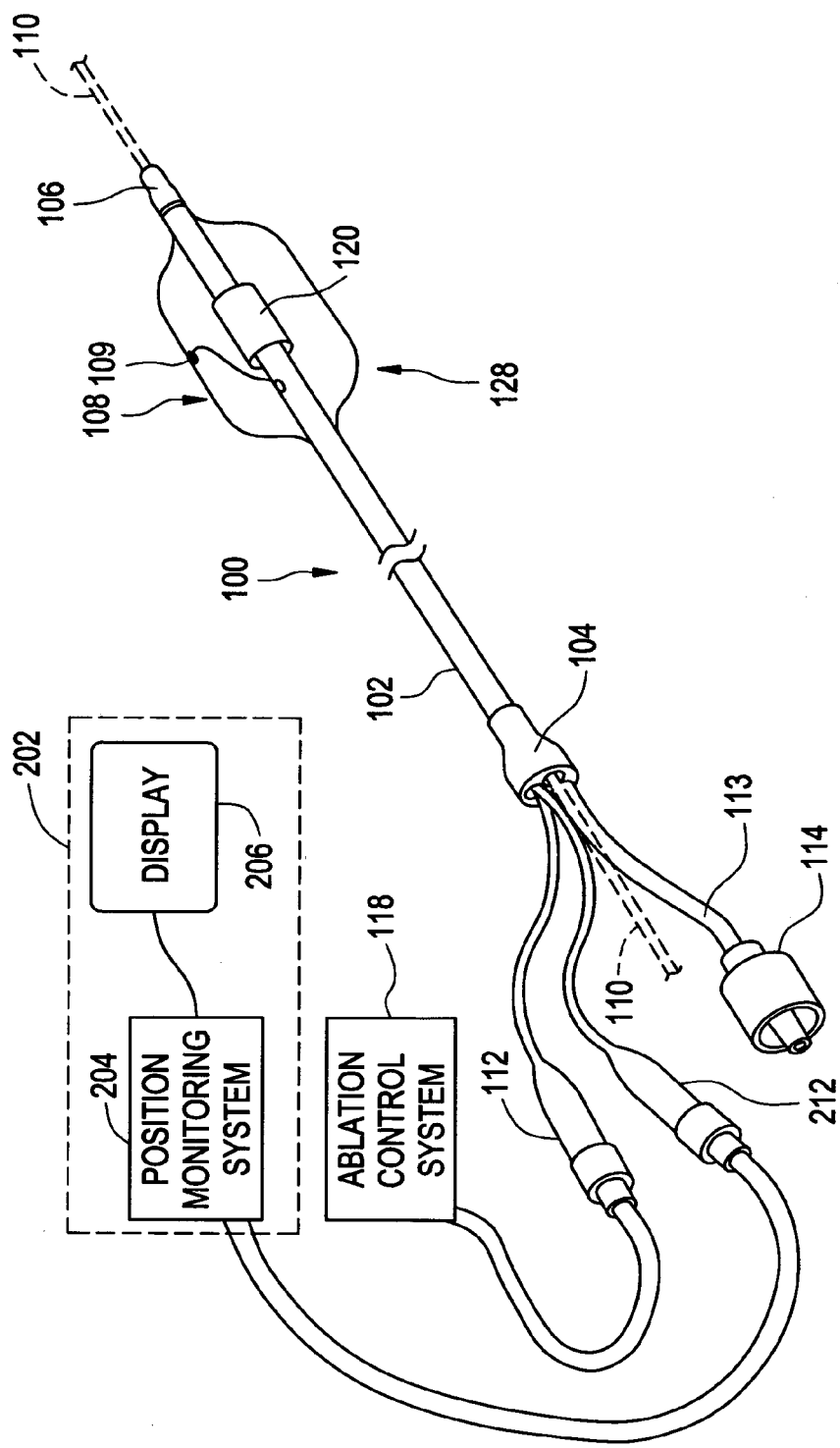

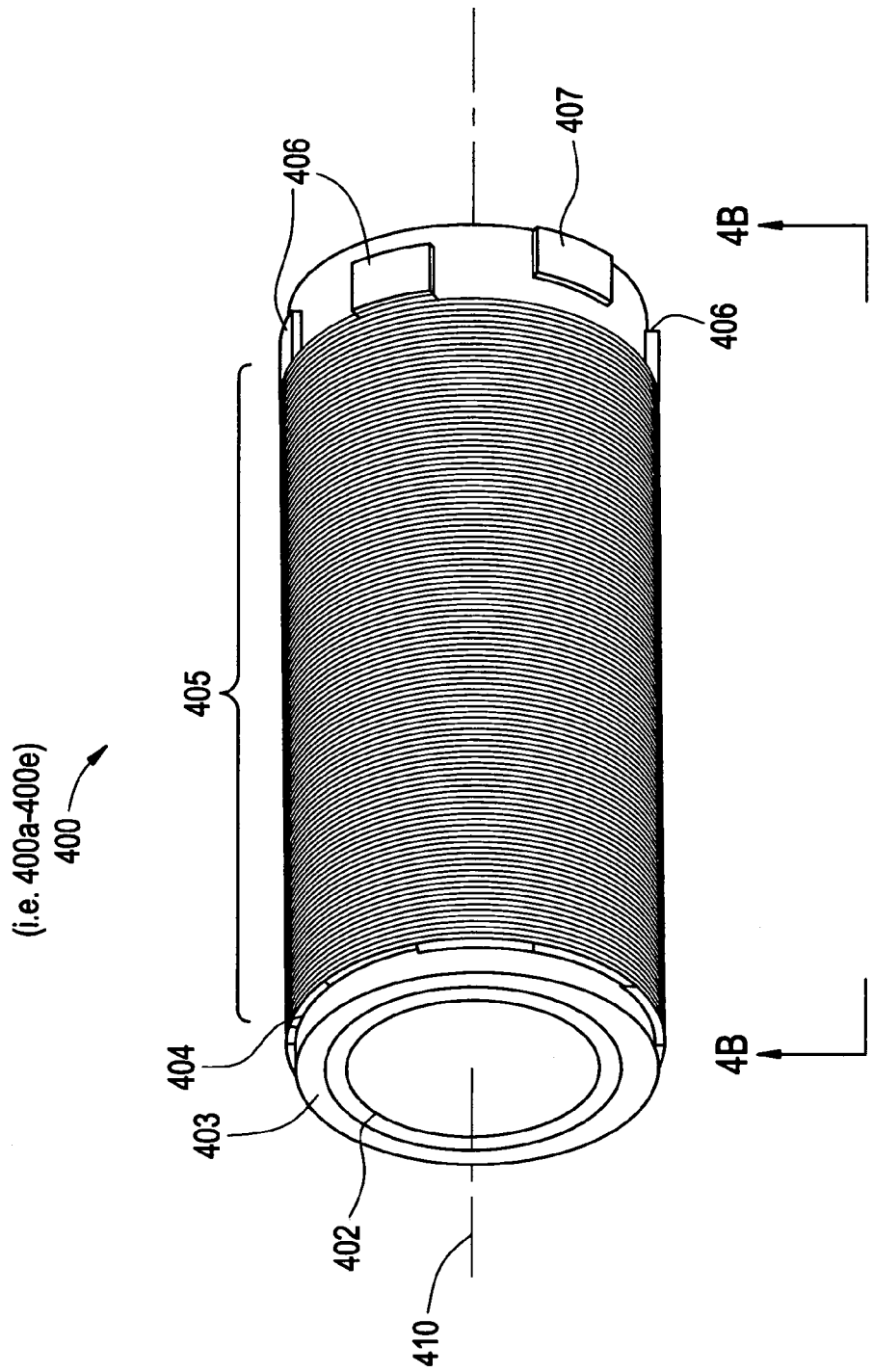

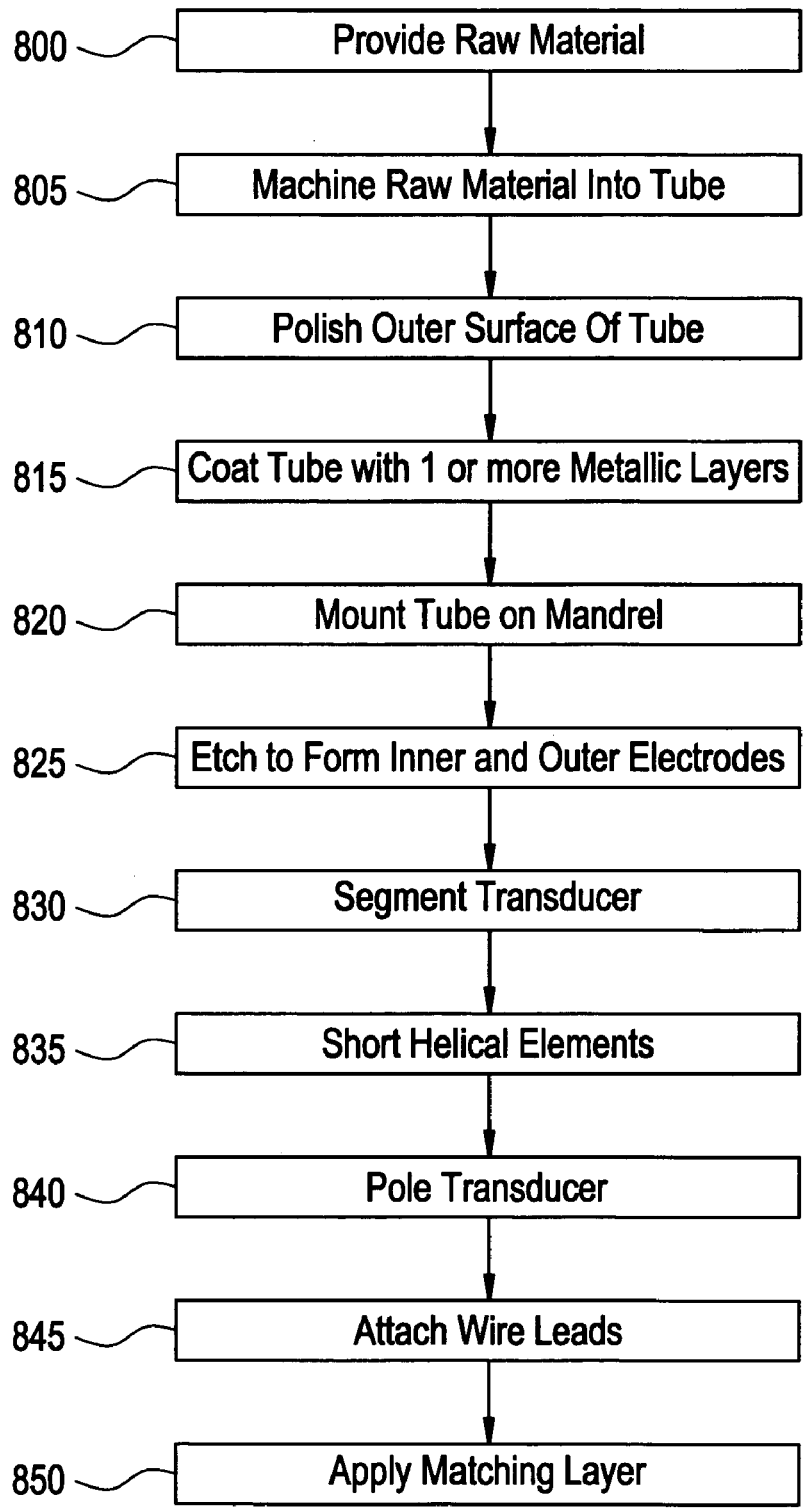

METHOD FOR MAKING A SPIRAL ARRAY ULTRASOUND TRANSDUCER

FIELD OF THE INVENTION

The present invention relates to a method for making a surgical device. More particularly, it relates to a method for making a tissue ablation transducer having a plurality of helical elements that can be operated out of phase to orient the acoustical energy beam forward or backward in the longitudinal direction.

BACKGROUND OF THE INVENTION

Many local energy delivery devices and methods have been developed for treating the various abnormal tissue conditions in the body, and particularly for treating abnormal tissue along body space walls that define various body spaces in the body. For example, various devices have been disclosed with the primary purpose of treating or recanalizing atherosclerotic vessels with localized energy delivery. Several prior devices and methods combine energy delivery assemblies in combination with cardiovascular stent devices in order to locally deliver energy to tissue in order to maintain patency in diseased lumens such as blood vessels. Endometriosis, another abnormal wall tissue condition that is associated with the endometrial cavity and is characterized by dangerously proliferative uterine wall tissue along the surface of the endometrial cavity, has also been treated by local energy delivery devices and methods. Several other devices and methods have also been disclosed which use catheter-based heat sources for the intended purpose of inducing thrombosis and controlling hemorrhaging within certain body lumens such as vessels. Detailed examples of local energy delivery devices and related procedures such as those of the types described above are disclosed in the following references: U.S. Pat. No. 4,672,962 to Hershenson; U.S. Pat. No. 4,676,258 to InoKuchi et al.; U.S. Pat. No. 4,790,311 to Ruiz; U.S. Pat. No. 4,807,620 to Strul et al.; U.S. Pat. No. 4,998,933 to Eggers et al.; U.S. Pat. No. 5,035,694 to Kasprzyk et al.; U.S. Pat. No. 5,190,540 to Lee; U.S. Pat. No. 5,226,430 to Spears et al.; and U.S. Pat. No. 5,292,321 to Lee; U.S. Pat. No. 5,449,380 to Chin; U.S. Pat. No. 5,505,730 to Edwards; U.S. Pat. No. 5,558,672 to Edwards et al.; and U.S. Pat. No. 5,562,720 to Stern et al.; U.S. Pat. No. 4,449,528 to Auth et al.; U.S. Pat. No. 4,522,205 to Taylor et al.; and U.S. Pat. No. 4,662,368 to Hussein et al.; U.S. Pat. No. 5,078,736 to Behl; and U.S. Pat. No. 5,178,618 to Kandarpa.

Other prior devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue-device interface either as another temperature control mechanism or in certain other known applications as a carrier or medium for the localized energy delivery. Detailed examples of ablation devices that use fluid to assist in electrically coupling electrodes to tissue are disclosed in the following references: U.S. Pat. No. 5,348,554 to Imran et al.; U.S. Pat. No. 5,423,811 to Imran et al.; U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.; U.S. Pat. No. 5,688,267 to Panescu et al.; U.S. Pat. No. 5,697,927 to Imran et al.; U.S. Pat. No. 5,722,403 to McGee et al.; U.S. Pat. No. 5,769,846; and PCT Patent Application Publication No. WO 97/32525 to Pomeranz et al.; and PCT Patent Application Publication No. WO 98/02201 to Pomeranz et al. Atrial Fibrillation.

Cardiac arrhythmias, and atrial fibrillation in particular, persist as common and dangerous medical aliments associated with abnormal cardiac chamber wall tissue, and are often observed in elderly patients. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction is known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self-propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. No. 4,641,649 to Walinsky et al. and in PCT Patent Application Publication No. WO 96/32897 to Desai.

A host of clinical conditions can result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle that thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, such as, for example, those approaches disclosed in the following references: U.S. Pat. No. 4,673,563 to Berne et al.; U.S. Pat. No. 4,569,801 to Molloy et al.; and "Current Management of Arrhythmias" (1991) by Hindricks, et al. Such pharmacological solutions, however, are not generally believed to be entirely effective in many cases, and are even believed in some cases to result in proarrhythmia and long term inefficacy.

Several surgical approaches have also been developed with the intention of treating atrial fibrillation. One particular example is known as the "maze procedure," as is disclosed by Cox, J. L. et al. in "The surgical treatment of atrial fibrillation. I. Summary" Thoracic and Cardiovascular Surgery 101(3), pp. 402-405 (1991); and also by Cox, J. L. in "The surgical treatment of atrial fibrillation. IV. Surgical Technique", Thoracic and Cardiovascular Surgery 101(4), pp. 584-592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium. See Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the region of the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the arrhythmogenic conduction from the boxed region of the pulmonary veins to the rest of the atrium by creating conduction blocks within the aberrant electrical conduction pathways. Other variations or modifications of this specific pattern just described have also been disclosed, all sharing the primary purpose of isolating known or suspected regions of arrhythmogenic origin or propagation along the atrial wall.

While the "maze" procedure and its variations as reported by Dr. Cox and others have met some success in treating patients with atrial arrhythmia, its highly invasive methodology is believed to be prohibitive in most cases. However, these procedures have provided a guiding principle that electrically isolating faulty cardiac tissue may successfully prevent atrial arrhythmia, and particularly atrial fibrillation caused by arrhythmogenic conduction arising from the region of the pulmonary veins.

Less invasive catheter-based approaches to treat atrial fibrillation have been disclosed which implement cardiac tissue ablation for terminating arrhythmogenic conduction in the atria. Examples of such catheter-based devices and treatment methods have generally targeted atrial segmentation with ablation catheter devices and methods adapted to form linear or curvilinear lesions in the wall tissue that defines the atrial chambers. Some specifically disclosed approaches provide specific ablation elements that are linear over a defined length intended to engage the tissue for creating the linear lesion. Other disclosed approaches provide shaped or steerable guiding sheaths, or sheaths within sheaths, for the intended purpose of directing tip ablation catheters toward the posterior left atrial wall such that sequential ablations along the predetermined path of tissue may create the desired lesion. In addition, various energy delivery modalities have been disclosed for forming atrial wall lesions, and include use of microwave, laser, ultrasound, thermal conduction, and more commonly, radiofrequency energies to create conduction blocks along the cardiac tissue wall.

Detailed examples of ablation device assemblies and methods for creating lesions along an atrial wall are disclosed in the following U.S. Patent references: U.S. Pat. No. 4,898,591 to Jang et al.; U.S. Pat. No. 5,104,393 to Isner et al.; U.S. Pat. Nos. 5,427,119; 5,487,385 to Avitall; U.S. Pat. No. 5,497,119 to Swartz et al.; U.S. Pat. No. 5,545,193 to Fleischman et al.; U.S. Pat. No. 5,549,661 to Kordis et al.; U.S. Pat. No. 5,575,810 to Swanson et al.; U.S. Pat. No. 5,564,440 to Swartz et al.; U.S. Pat. No. 5,592,609 to Swanson et al.; U.S. Pat. No. 5,575,766 to Swartz et al.; U.S. Pat. No. 5,582,609 to Swanson; U.S. Pat. No. 5,617,854 to Munsif; U.S. Pat. No. 5,687,723 to Avitall; U.S. Pat. No. 5,702,438 to Avitall. Other examples of such ablation devices and methods are disclosed in the following PCT Patent Application Publication Nos.: WO 93/20767 to Stern et al.; WO 94/21165 to Kordis et al.; WO 96/10961 to Fleischman et al.; WO 96/26675 to Klein et al.; and WO 97/37607 to Schaer. Additional examples of such ablation devices and methods are disclosed in the following published articles: "Physics and Engineering of Transcatheter Tissue Ablation". Avitall et al., Journal of American College of Cardiology, Volume 22, No. 3:921-932 (1993); and "Right and Left Atrial Radiofrequency Catheter Therapy of Paroxysmal Atrial Fibrillation," Haissaguerre, et al., Journal of Cardiovascular Electrophysiology 7(12), pp. 1132-1144 (1996).

In addition to those known assemblies summarized above, additional tissue ablation device assemblies have been recently developed for the specific purpose of ensuring firm contact and consistent positioning of a linear ablation element along a length of tissue by anchoring the element at least at one predetermined location along that length, such as in order to form a "maze"-type lesion pattern in the left atrium. One example of such assemblies is that disclosed in U.S. Pat. No. 5,971,983, issued Oct. 26, 1999, which is hereby incorporated by reference. The assembly includes an anchor at each of two ends of a linear ablation element in order to secure those ends to each of two predetermined locations along a left atrial wall, such as at two adjacent pulmonary veins, so that tissue may be ablated along the length of tissue extending there between.

In addition to attempting atrial wall segmentation with long linear lesions for treating atrial arrhythmia, other ablation device and method have also been disclosed which are intended to use expandable members such as balloons to ablate cardiac tissue. Some such devices have been disclosed primarily for use in ablating tissue wall regions along the cardiac chambers. Other devices and methods have been disclosed for treating abnormal conduction of the left-sided accessory pathways, and in particular associated with "Wolff-Parkinson-White" syndrome—various such disclosures use a balloon for ablating from within a region of an associated coronary sinus adjacent to the desired cardiac tissue to ablate. Further more detailed examples of devices and methods such as of the types just described are variously disclosed in the following published references: Fram et al., in "Feasibility of RF Powered Thermal Balloon Ablation of Atrioventricular Bypass Tracts via the Coronary Sinus: In vivo Canine Studies," PACE, Vol. 18, p 1518-1530 (1995); "Long-term effects of percutaneous laser balloon ablation from the canine coronary sinus", Schuger CD et al., Circulation (1992) 86:947-954; and "Percutaneous laser balloon coagulation of accessory pathways", McMath L P et al., Diagn Ther Cardiovasc Interven 1991; 1425:165-171.

Arrhythmias Originating from Foci in Pulmonary Veins

Various modes of atrial fibrillation have also been observed to be focal in nature, caused by the rapid and repetitive firing of an isolated center within cardiac muscle tissue associated with the atrium. Such foci may act as either a trigger of atrial fibrillatory paroxysmal or may even sustain the fibrillation. Various disclosures have suggested that focal atrial arrhythmia often originates from at least one tissue region along one or more of the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to terminate the inappropriate arrhythmogenic conduction.

One example of a focal ablation method intended to treat focal arrhythmia originating from a pulmonary vein is disclosed by Haissaguerre, et al. in "Right and Left Atrial Radiofrequency Catheter Therapy of Paroxysmal Atrial Fibrillation" in Journal of Cardiovascular Electrophysiology 7(12), pp. 1132-1144 (1996). Haissaguerre, et al. discloses radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and the focal ablations were generally performed using a standard 4 mm tip single ablation electrode.

Another focal ablation method of treating atrial arrhythmias is disclosed in Jais et al., "A focal source of atrial fibrillation treated by discrete radiofrequency ablation," Circulation 95:572-576 (1997). Jais et al. discloses treating patients with paroxysmal arrhythmias originating from a focal source by ablating that source. At the site of arrhythmogenic tissue, in both right and left atria, several pulses of a discrete source of radiofrequency energy were applied in order to eliminate the fibrillatory process.

Other assemblies and methods have been disclosed addressing focal sources of arrhythmia in pulmonary veins by ablating circumferential regions of tissue either along the pulmonary vein, at the ostium of the vein along the atrial wall, or encircling the ostium and along the atrial wall. More detailed examples of device assemblies and methods for treating focal arrhythmia as just described are disclosed in PCT Patent Application Publication No. WO 99/02096 to Diederich et al., and also in the following pending U.S. patent and patent applications: U.S. Pat. No. 6,024,740, issued on Feb. 15, 2000 to Michael D. Lesh et al., for "Circumferential Ablation Device Assembly"; U.S. Pat. No. 6,012,457, issued on Jan. 11, 2000 to Michael D. Lesh, for "Device and Method for Forming a Circumferential Conduction Block in a Pulmonary Vein"; U.S. Pat. No. 6,117,101 issued on Sep. 12, 2000 to Chris J. Diederich et al., for "Circumferential Ablation Device Assembly"; and U.S. Ser. No. 09/260,316 for "Device and Method for Forming a Circumferential Conduction Block in a Pulmonary Vein" to Michael D. Lesh.

Another specific device assembly and method which is intended to treat focal atrial fibrillation by ablating a circumferential region of tissue between two seals in order to form a conduction block to isolate an arrhythmogenic focus within a pulmonary vein is disclosed in U.S. Pat. No. 5,938,660 and a related PCT Patent Application Publication No. WO 99/00064.

SUMMARY OF THE INVENTION

The present invention relates to a method for making a device assembly and tissue ablation transducer having a plurality of helical elements that can be operated out of phase to orient the acoustical energy beam forward or backward in the longitudinal direction. In one embodiment of the invention the method for making a piezoelectric transducer comprises first providing a ceramic material blank, and machining the blank into a tubular configuration. The ceramic tube is coated with a metallic layer. The metal coated ceramic tube is then machined to form an inner electrode and a series of helically intertwined outer electrodes, each outer electrode being associated with a transducer segment. The ceramic material is transformed into a piezoelectric crystal, thus forming a transducer with a series of intertwined individual helical transducer segments.

In another embodiment of the present invention, a method of making a piezoelectric transducer, having a plurality of transducer segment, from a PZT ceramic tube comprises coating the inside and outside of the ceramic tube with a metallic layer. In pertinent part, this step forms an inner electrode and an outer electrode. At least the outer electrode is then etched to form a plurality of intertwined helical transducer segments.

In still another embodiment of the present invention, a method of making an ultrasound transducer with a helical phased array comprises providing a cylindrical piezoelectric transducer having a piezoelectric material disposed between a cylindrical inner electrode and a cylindrical outer electrode. Grooves are then machined through at least the outer electrode to segment the transducer into a plurality of functionally discrete intertwined helical transducer segments.

BRIEF DESCRIPTION OF THE DRAWINGS

FIG. 2A is a perspective view showing an ablation catheter operably connected to an ablation control system and a position sensing system according to one embodiment of the present invention. An expandable member of the catheter is illustrated in an expanded state.

FIG. 4A is a perspective view showing the construction of a transducer sectioned into a spiral array of ultrasonic transducer segments according to one embodiment of the present invention.

FIG. 8 is a flow diagram illustrating the method for making a transducer having a plurality of helical transducer elements according to one embodiment of the present invention.

DETAILED DESCRIPTION OF THE INVENTION

Definitions of Terms

Figure 1A:
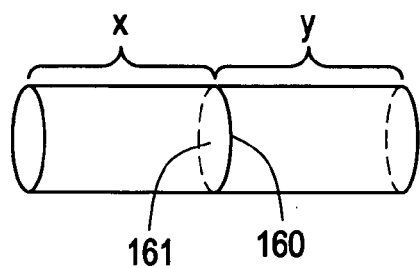
FIG. 1A is a perspective representation showing an example of a circular ablation path.
Figure 1B:
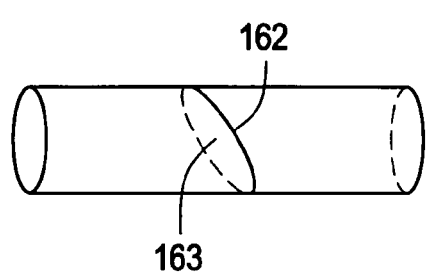
FIG. 1B is a perspective representation showing an example of an elliptical ablation path.
Figure 1C:
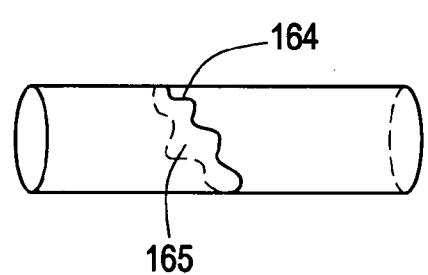
FIG. 1C is a perspective representation showing an example of an irregular ablation path.
Figure 1D:
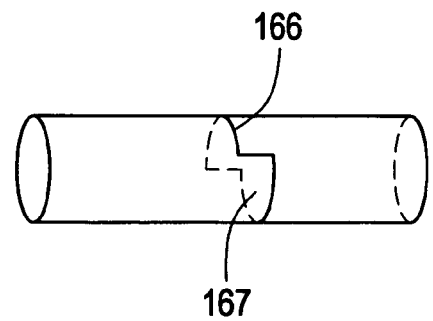
FIG. 1D is a perspective representation showing an example of a stepped ablation path.

The following terms will have the following meanings throughout this specification.

The terms "body space," including derivatives thereof, is herein intended to mean any cavity or lumen within the body that is defined at least in part by a tissue wall. For example, the cardiac chambers, the uterus, the regions of the gastrointestinal tract, and the arterial or venous vessels are all considered illustrative examples of body spaces within the intended meaning.

The terms "circumference" or "circumferential", including derivatives thereof, as used herein include a continuous path or line that forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, as used herein includes a surface to enclose, surround, or encompass a defined region of space. Therefore, a continuous line which is traced around a region of space and which starts and ends at substantially the same location "circumscribes" the region of space and has a "circumference" which includes the distance the line travels as it translates along the path circumscribing the space.

Still further, a circumferential path or element may include one or more of several shapes, and may be for example circular, oblong, ovular, elliptical, or otherwise planar enclosures. A circumferential path may also be three dimensional, such as for example two opposite-facing semicircular paths in two different parallel or off-axis planes that are connected at their ends by line segments bridging between the planes.

For purpose of further illustration and example, FIGS. 1A-1D show circumferential paths 160, 162, 164, and 166, respectively. Each path 160, 162, 164, 166 translates along a portion of a body space, for example a pulmonary vein wall, and circumscribes a defined region of space, shown at 161, 163, 165, and 167, respectively, each circumscribed region of space being a portion of the body space. However, the circumferential path does not necessarily have to be translate along a tubular structure as shown, and other geometric structures are also contemplated, such as along the atrial wall in the atrium of a heart.

The term "transect", including derivatives thereof, as used herein includes a way to divide or separate a region of space into isolated regions. Thus, each of the regions circumscribed by the circumferential paths shown in FIGS. 1A-D transects the respective body space, for example the pulmonary vein, including its lumen and its wall, to the extent that the respective body space is divided into a first longitudinal region located on one side of the transecting region, shown for example at region "X" in FIG. 1A, and a second longitudinal region on the other side of the transecting plane, shown for example at region "Y" also in FIG. 1A. Similarly, a circumferential path along other structures, such as the atrial wall around the pulmonary vein ostium will transect the pulmonary vein from the atrium.

Therefore, a "circumferential conduction block" according to the present invention is formed along a region of tissue that follows a circumferential path, circumscribing the tissue region and transecting the region of tissue relative to electrical conduction along the circumferential path. By way of example, the transecting circumferential conduction block therefore isolates electrical conduction between the left atrium and a pulmonary vein.

The terms "ablate" or "ablation," including derivatives thereof, are hereafter intended to include the substantial altering of the mechanical, electrical, chemical, or other structural nature of tissue. In the context of ablation applications shown and described with reference to the variations of the illustrative device below, "ablation" is intended to include sufficient altering of tissue properties to substantially block conduction of electrical signals from or through the ablated cardiac tissue.

The term "element" within the context of "ablation element" is herein intended to include a discrete element, such as an ultrasonic transducer, or a plurality of discrete elements, such as a plurality of spaced ultrasonic transducers, which are positioned so as to collectively ablate a region of tissue.

Therefore, an "ablation element" according to the defined terms can include a variety of specific structures adapted to ablate a defined region of tissue. For example, one suitable ablation element for use in the present invention may be formed, according to the teachings of the embodiments below, from an "energy emitting" type of structure which is adapted to emit energy sufficient to ablate tissue when coupled to and energized by an energy source. One particular suitable "energy emitting" ablation element for use in the present invention may therefore include, for example an ultrasonic element such as an ultrasound crystal element which is adapted to emit ultrasonic sound waves sufficient to ablate tissue when coupled to a suitable excitation source.

EMBODIMENTS OF THE INVENTION

The following describes ablation devices of a medical device system. The disclosed devices may include a position monitoring system that allows a clinician to precisely locate a distal end of the medical device within a body space by using feedback information provided by the system. Such feedback information is indicative of the position of the distal end of the medical device within the body space. The following devices of the position monitoring system are particularly well suited for applications involving positioning an ablation member at an area where a pulmonary vein extends from a left atrium and relative to a targeted circumferential region of tissue within the area, and therefore these devices are described in this context. Various aspects of the present invention, however, can be readily adapted by those skilled in the art for applications involving positioning medical articles within other body spaces.

In the context of the illustrative application, catheter-based cardiac arrhythmia therapies generally involve introducing an ablation catheter into a cardiac chamber, such as in a percutaneous transluminal procedure, wherein an ablation element on the catheter's distal end portion is positioned at or adjacent to the aberrant conductive tissue. The ablation element is used to ablate the targeted tissue thereby creating a lesion.

FIG. 2A shows an exemplary ablation catheter assembly 100 operably connected through an electrical connector 112 to an ablation control system 118. The catheter assembly 100 includes an elongated delivery member 102 with a proximal end portion 104 and a distal end portion 106. The distal end portion 106 supports an ablation member 128 including an ablation element 120 and an anchor mechanism 108. In one preferred embodiment (illustrated in FIG. 2A), the anchor mechanism 108 is an expandable member. The expandable member can also include a sensor 109 that is explained below.

Figure 2B:
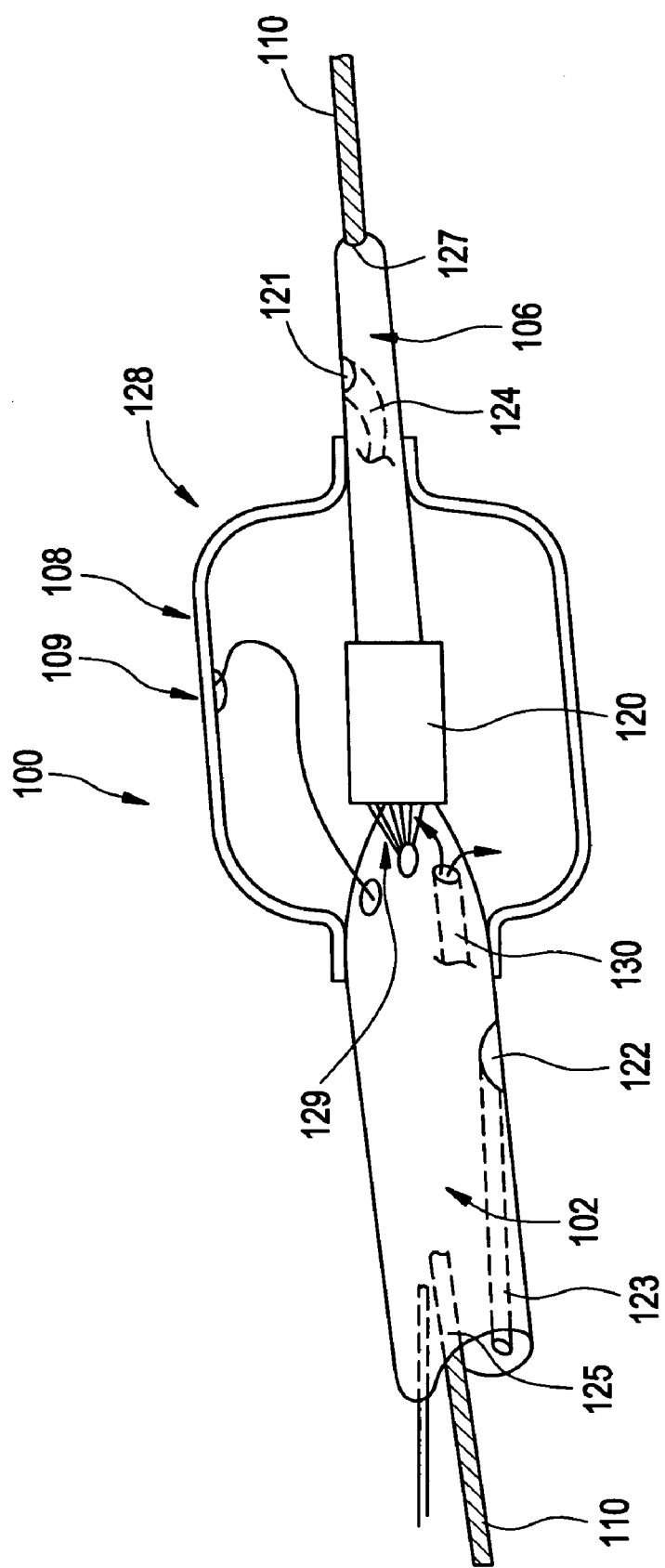
FIG. 2B is a perspective view showing the details of an ablation member in the expanded state at a distal end of the ablation catheter of FIG. 2A according to one embodiment of the present invention.

The delivery member 102 desirably includes a plurality of lumens (some of which are illustrated in FIG. 2B). Various wires and electrical leads are routed to the distal end portion 106 through at least some of these lumens. In a preferred device, these lumens generally run the length of the delivery member 102; however, for some applications, the lumens can be shorter. In one example, a guidewire 110 runs through a lumen in the delivery member 102 from the proximal end portion 104 to the distal end portion 106. The proximal end portion 104 also connects through a tube 113 to a screw connector 114. By introducing fluid into the tube 113 through the screw connector 114, a physician can inflate the expandable member 108, as known in the art.

In some modes of the catheter assembly, as seen in FIG. 2B, the delivery member 102 includes a distal port 121, which is distal to an ablation member 128. In addition, there is a proximal port 122, which is provided proximal of the ablation member 128. The proximal port 122 connects to a proximal port lumen 123, and the distal port 121 connects to a distal port lumen 124. The distal port 121 allows the clinician to introduce fluids into the patient, take fluid samples from the patient, and take fluid pressure reading on the distal side of the ablation member 128. Similarly, the proximal port 122 allows the clinician to introduce fluids into the patient, take fluid samples from the patient, and take fluid pressure reading on the proximal side of the ablation member 128. These ports 121, 122 and lumens 123 and 124 are particularly useful when pressure or X-ray positioning techniques are employed, as explained below; however, the catheter assembly 100 need not include such ports and lumens when only an A-mode or Doppler position monitoring system is used with the catheter assembly.

In the illustrated device, the delivery member 102 also includes a guidewire lumen 125 that is sized to track over the guidewire 110. The lumen 125 terminates at a distal port 127 located on the distal end 106 of the delivery member 102.

When constructed for use in transeptal left atrial ablation procedures, the delivery member 102 desirably has an outer diameter provide within the range of from about 5 French to about 10 French, and more preferably from about 7 French to about 9 French. The guidewire lumen 125 preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen 125 preferably has an inner diameter of 0.040 inch to about 0.042 inch. In addition, where the delivery member 102 includes an inflation lumen 130 for use with an inflatable balloon (a preferred form of the expandable member 108), the inflation lumen 130 preferably has an inner diameter of about 0.020 inch in order to allow for rapid deflation times, although this may vary based upon the viscosity of inflation medium used, length of the lumen 130, and other dynamic factors relating to fluid flow and pressure.

In addition to providing the requisite lumens and support for the ablation member 128, the delivery member 102 for the illustrative application also is adapted to be introduced into the left atrium such that the distal end portion 106 can be placed within the pulmonary vein ostium in a percutaneous translumenal procedure, and even more preferably in a transeptal procedure as otherwise herein provided. Therefore, the distal end portion 106 is preferably flexible and adapted to track over and along a guidewire seated within the targeted pulmonary vein.

In a further construction, the proximal end portion 104 is adapted to be at least 30% more stiff than the distal end portion 106. According to this relationship, the proximal end portion 104 may be suitably adapted to provide push transmission to the distal end portion 106 while the distal end portion 106 is suitably adapted to track through bending anatomy during in vivo delivery of the distal end portion 106 of the device into the desired ablation region.

Notwithstanding the specific device constructions just described, other delivery mechanisms for delivering the ablation member 128 to the desired ablation region are also contemplated. For example, while the FIG. 2A variation is shown as an "over-the-wire" catheter construction, other guidewire tracking designs are suitable substitutes, such as, for example, catheter devices that are known as "rapid exchange" or "monorail" variations, wherein the guidewire is only housed coaxially within a lumen of the catheter in the distal region of the catheter. In another example, a deflectable tip design may also be a suitable substitute to independently select a desired pulmonary vein and direct the transducer assembly into the desired location for ablation.

Further to this latter variation, the guidewire lumen and guidewire of the variation depicted in FIG. 2A may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

As discussed above, the distal end portion 106 of the delivery member supports an ablation member 128. The ablation member 128 includes an expandable member 108 and an ablation element 120. The expandable member 108 cooperates with the ablation element 120 to position and anchor the ablation element 120 relative to a circumferential region of tissue. Regions of tissue targeted for ablation may include, for example, a location where a pulmonary vein extends from the left atrium, including the back atrial wall of the left atrium, the pulmonary vein ostium or the pulmonary vein.

In the illustrated device, the expandable member 108 is an inflatable balloon. The balloon has a diameter in a collapsed state roughly the same as the outer diameter of the delivery member distal end portion 106. The balloon 108 can be expanded to a diameter generally matching the diameter of the circumferential region of tissue, and may be expandable to a plurality of expanded positions in order to work with pulmonary vein ostia and/or pulmonary veins of various sizes. It is understood, however, that the ablation catheter assembly can also include other types of expandable members, such as, for example baskets, cages and like expandable structures.

The expandable balloon 108 may be constructed from a variety of known materials, although the balloon preferably is adapted to conform to the contour of a pulmonary vein ostium and/or pulmonary vein lumenal wall. For this purpose, the balloon material can be of the highly compliant variety, such that the material elongates upon application of pressure and takes on the shape of the body lumen or space when fully inflated. Suitable balloon materials include elastomers, such as, for example, but without limitation, silicone, latex, or low durometer polyurethane (for example a durometer of about 80 A).

In addition, or in the alternative to constructing the balloon of highly compliant material, the balloon can be formed to have a predefined fully inflated shape (i.e., be preshaped) to generally match the anatomic shape of the body lumen in which the balloon is inflated. For instance, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taut configuration. In other words, "expansion" is herein intended to relate to the change in diameter that is attributable to the material compliance in a stress/strain relationship. In one more detailed construction, which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion).

The ablation element 120 cooperates with the expandable member 108 such that the ablation element 120 is held in a generally fixed position relative to the target circumferential region of tissue. The ablation element can be located outside or inside the expandable member, or can be located at least partially outside the expandable member. The ablation element, in some forms, also includes a portion of the expandable member. For instance, the ablation catheter assembly in FIGS. 2A and 2B includes an ultrasonic transducer located within the expandable member 108. In one device, the ultrasonic transducer excites a portion of the expandable member 108 during ablation. The specific construction of the ultrasonic transducer and the associated construction of the delivery member shaft that supports the transducer, is described below.

FIG. 2B shows details of the distal end portion 106 of the catheter assembly 100 and, in particular, shows the ablation element 120 located circumferentially about an axial centerline of the delivery member 102. A plurality of wires 129 connect the ablation element 120 to a connector 112 at the proximal end of the catheter (shown in FIG. 2A). The connector 112 is coupled to a corresponding cable of the ablation control system 118. If the ablation element 120 includes more than one electrode, the conductor lead can connect to all of the electrodes or energy sources, or separate conductors can be used so as to allow for independent control of each electrode or energy source under some modes of operation.

Figure 3A:
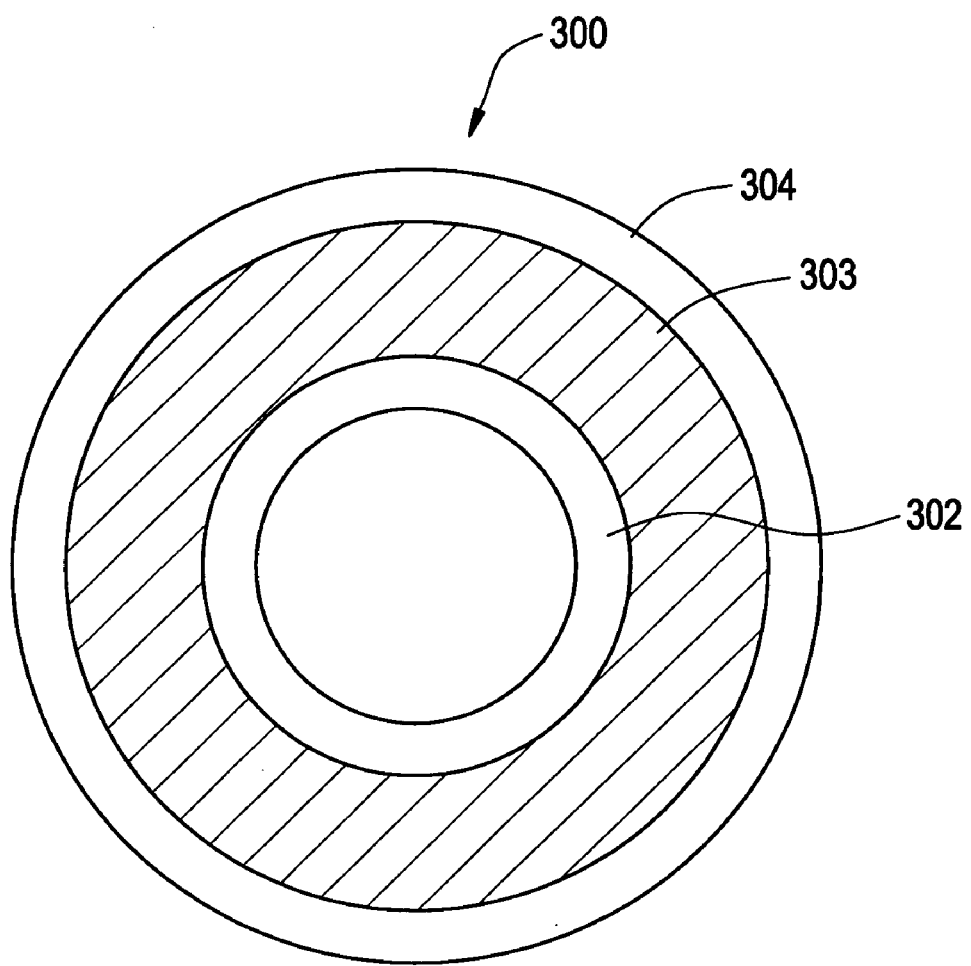
FIG. 3A is a transverse cross-section view showing the construction of a typical prior art cylindrical ultrasonic transducer having inner and outer electrodes.

A cross-section view showing construction of a typical single cylindrical ultrasonic transducer 300 having a cylindrical inner electrode 302, a cylindrical outer electrode 304, and a cylindrical piezoelectric material 303 between the electrodes is shown in FIG. 3A. The piezoelectric material 303 is a suitable material, such as, for example quartz, PZT, and the like, that exhibits a change in physical dimension in response to an impressed voltage. The piezoelectric material 303 is oriented such that when a voltage is impressed between the electrodes 302 and 304, the thickness of the piezoelectric material 303 changes slightly. When the polarity of the impressed voltage is alternated at an ultrasonic frequency F, the piezoelectric material 303 will vibrate at the ultrasonic frequency F. The vibrations of the piezoelectric material 303 produce ultrasonic sound waves. Since the electrodes are cylindrically symmetric, the piezoelectric material 303 will vibrate radially, with cylindrical symmetry. Conversely, when an ultrasonic wave hits the piezoelectric material 303, the ultrasonic wave will cause vibrations in the piezoelectric material. These vibrations will generate a voltage between the electrodes 302 and 304. Thus, the transducer is a reciprocal device that can both transmit and receive ultrasonic waves.

Figure 3B:
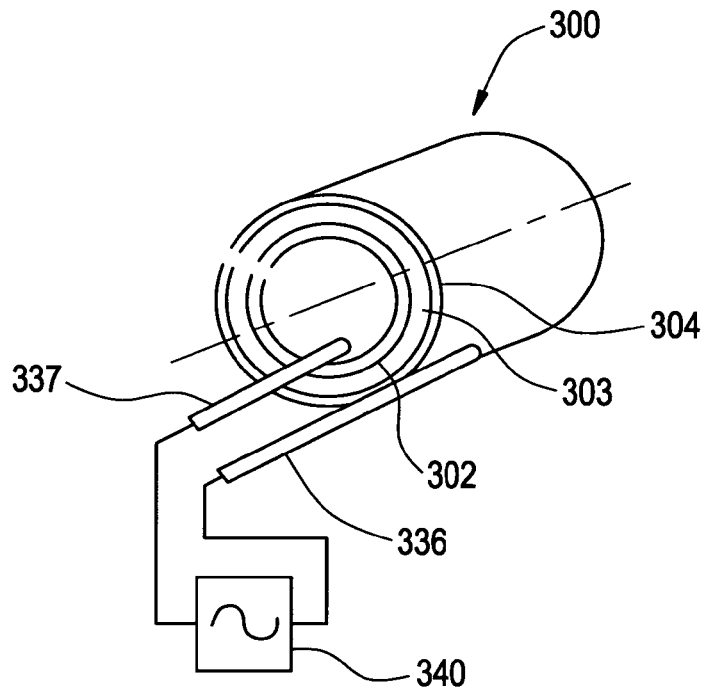
FIG. 3B is a perspective view of a typical prior art ultrasound transducer in isolation, showing the electrical leads coupled to the transducer.
Figure 3C:
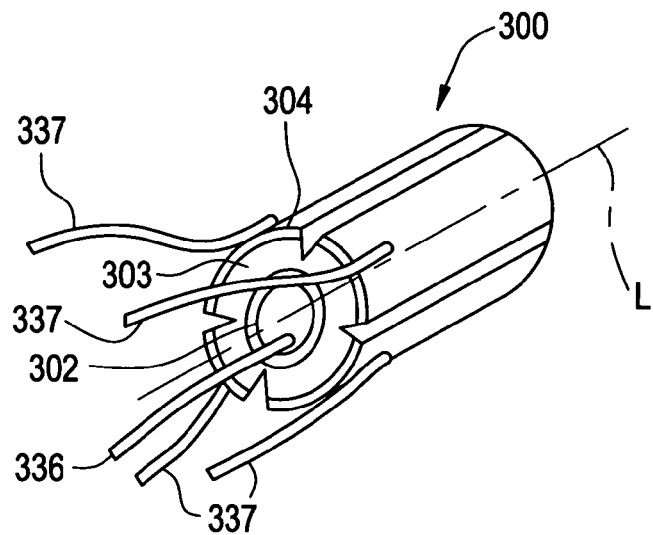
FIG. 3C is a perspective view of a prior art ultrasound transducer with individually driven sectors.

A detailed construction for a cylindrical ultrasound transducer is shown in FIGS. 3B and 3C. The length of the transducer 300 or transducer assembly (e.g., multi-element array of transducer elements) desirably is selected for a given clinical application. In connection with forming circumferential condition blocks in cardiac or pulmonary vein wall tissue, the transducer length can fall within the range of approximately 80 mils up to greater than 395 mils, and preferably equals about 200 mils to 295 mils. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer 300 preferably has an outer diameter within the range of about 70 mils to greater than 100 mils. It has been observed that a transducer with an outer diameter of about 80 mils generates acoustic power levels approaching 20 Watts per centimeter radiator or greater within myocardial or vascular tissue, which is believed to be sufficient for ablation of tissue engaged by the outer balloon for up to about 1.4 inches (3.5 cm) outer diameter of the balloon. For applications in other body spaces, the transducer 300 may have an outer diameter within the range of about 40 mils to greater than 120 to 160 mils (e.g., as large as 400 to 800 mils for applications in some body spaces).

The central crystal layer 303 of the transducer 300 has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer 300 in the illustrated application preferably operates within the range of about 5 MHz to about 20 MHz, and more preferably within the range of about 7 MHz to about 10 MHz. Thus, for example, the transducer can have a thickness of approximately 12 mils for an operating frequency of about 7 MHz (i.e., a thickness generally equal to ½ the wavelength associated with the desired operating frequency).

The transducer 300 is vibrated across the wall thickness and to radiate collimated acoustic energy in the radial direction. For this purpose the distal ends of electrical leads 336, 337 are electrically coupled to outer and inner tubular members or electrodes 304, 302, respectively, of the transducer 300, such as, for example, by soldering the leads to the metallic coatings or by resistance welding. In the illustrated device, the electrical leads are 4-8 mil (0.004 to 0.008 inch diameter) silver wire or the like. The proximal ends of these leads are adapted to couple to an ultrasonic driver or actuator 340, which is schematically illustrated in FIG. 3B.

Figure 3D:
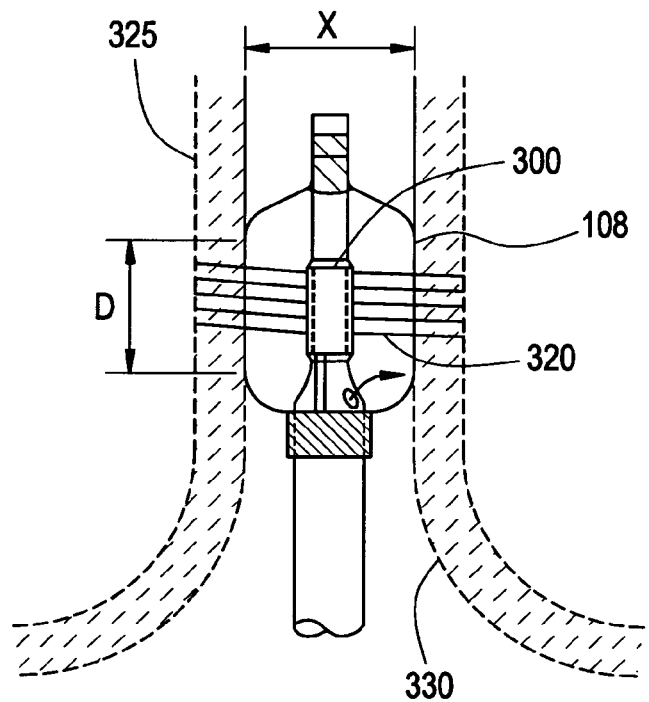
FIG. 3D is a side view of a prior art ablation catheter showing the collimated radial acoustical energy beam paths when the ablation device is place in a body lumen, such as a pulmonary vein.
Figure 3E:
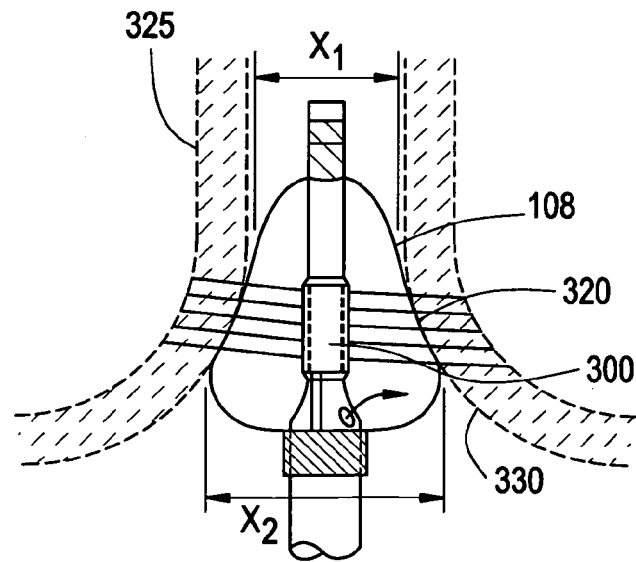
FIG. 3E is a side view of a prior art ablation catheter showing the collimated radial acoustical energy beam paths when the ablation device is placed at the juncture between a body lumen and a body cavity, such as a pulmonary vein ostium.

The transducer 300 also can be sectored by etching or notching grooves in the outer transducer electrode 304 and part of the central piezoelectric crystal layer 303 along lines parallel to the longitudinal axis L of the transducer 300, as illustrated in FIG. 3C. The sectoring substantially electrically isolates the outer transducer electrode 304, creating in effect separate transducers. A separate electrical lead connects to each sector in order to couple the sector to a dedicated power control that individually excites the corresponding transducer sector. By controlling the driving power and operating frequency to each individual sector, the ultrasonic driver 340 can enhance the uniformity of the acoustic energy beam around the transducer 300, as well as can vary the degree of heating (i.e., lesion control) in the angular dimension. However, in this configuration, the acoustic energy remains highly collimated in the radial direction, and does not allow the acoustical beam to be projected forward or backward. FIGS. 3D and 3E illustrate the collimated radial acoustical energy beam paths 320 when the ablation device is placed in a pulmonary vein 325 and pulmonary vein ostium 330, respectively.

The present invention utilizes a tissue ablation element and device assembly capable of creating a circular energy beam that can be phased in the longitudinal direction, orienting the beam forward or backward. In one embodiment of the invention the ablation element is a thin wall ultrasonic transducer sectioned into a small number of intertwined helical transducer segments with many turns forming a spiral array.

Figure 4B:
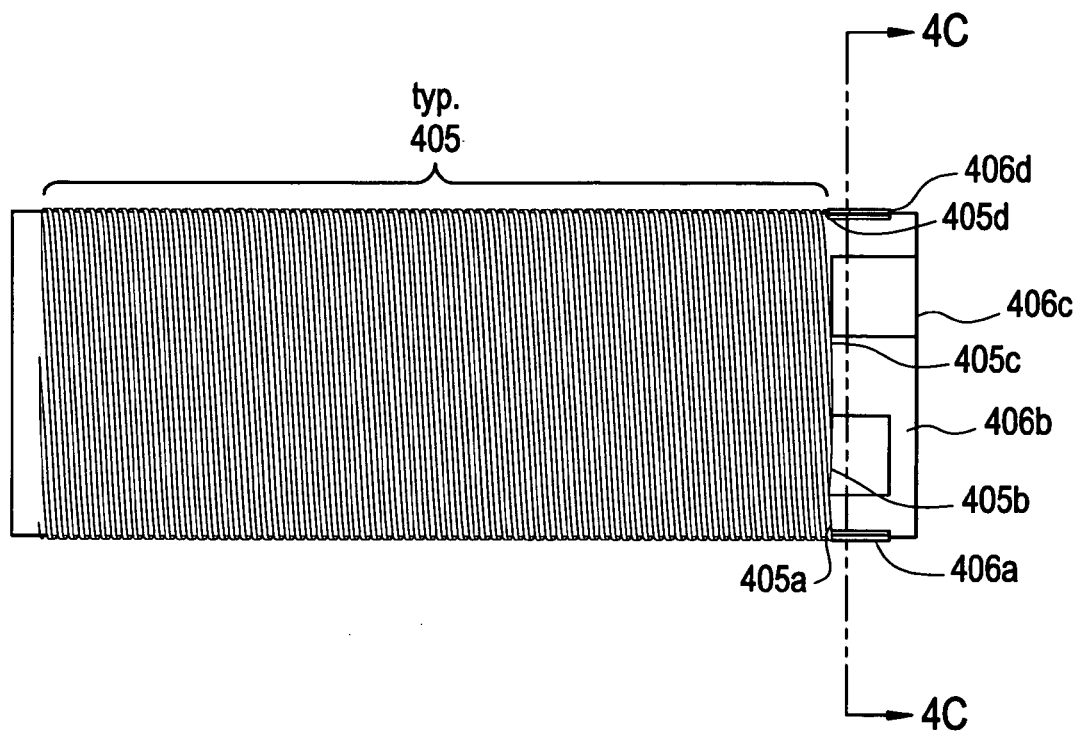
FIG. 4B is a side view showing the construction of a transducer sectioned into a spiral array of ultrasonic transducer segments according to one embodiment of the present invention.
Figure 4C:
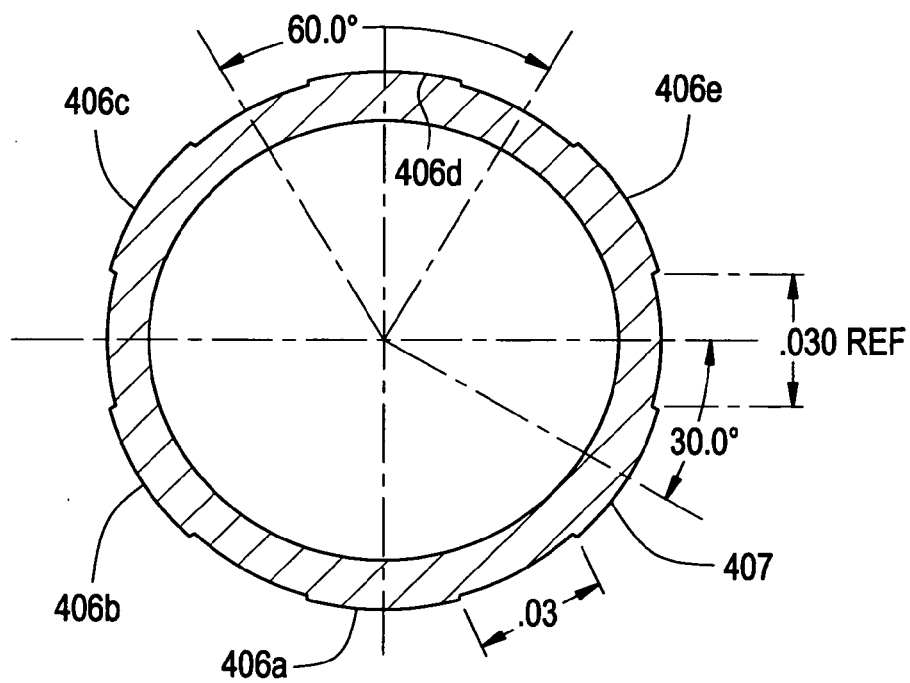
FIG. 4C is an end view showing the construction of a transducer sectioned into a spiral array of ultrasonic transducer segments according to one embodiment of the present invention.

FIG. 4A through 4C are perspective, side and end views, respectively, showing the construction of a spiral array of ultrasonic transducers segments according to one embodiment of the present invention. The array is made from a single tube shaped piezoelectric transducer 400 having a longitudinal axis 410. The transducer 400 comprises a piezoelectric crystal 403 between an inner electrode 402, and an outer electrode 404. The transducer 400 is approximately 325 mils long with an outside diameter of approximately 100 mils, and a wall thickness of approximately 18 mils.

The outer electrode 404 is segmented by etched grooves into a small number of intertwined individual helical elements 405 having a plurality of turns. Each individual element 405 is substantially electrically insulated from the other elements, allowing the segmented elements to operate independently with minimal interference. This configuration in effect essentially forms an array of helically shaped functionally discrete transducers arranged linearly along the longitudinal axis 410. Hereinafter, these apparent functionally discrete transducers will be referred to as transducer segments. When operated out of phase, the helical phased array configuration allows the transducer 400 to achieve a phase coherency equal to many more individual serially phased transducers placed axially along the longitudinal axis 410. For the purpose of example, the illustrated embodiment shows a transducer 400 having an outer electrode 404 sectored into five (5) elements 405 (405a through 405e) corresponding to five (5) discrete transducer segments 400a through 400e. Each transducer segment 400a through 400e encompasses twenty (20) turns, providing the phasing coherency of approximately one hundred (100) separate phased transducers arranged serially along the longitudinal axis 410.

The number of elements 405, transducer segments (400a through 400e), and turns illustrated is exemplary. One of skill in the art would understand that other configurations are contemplated by the present invention having more or fewer helical elements 405. Several factors, including the desired application, may contribute to these other configurations.

Each individual helical element 405 has an enlarged element pad 406 (406a through 406e) that serves as a connection point for the lead wires (not shown) used to energize the individual transducer segments (400a through 400e respectively). Each of these element pads 406 is substantially electrically insulated from one another to limit interference between individual elements 405. In addition, a ground pad 407 is attached to the inner electrode 402 and provides a connection point for a ground wire.

The illustrated embodiment has six (6) pads (five element pads 406a-406e and one ground pad 407). Each pad is equally spaced around the circumference of the transducer 400, approximately sixty (60) degrees from each other. However, this configuration should not be read to limit the scope of the invention. Instead, it is only necessary that each element pad 406 be substantially electrically insulated from one another other to minimize interference and cross-talk between elements 405, regardless of the configuration.

In a preferred embodiment, attachment of the lead and ground wires is by soldering the wires directly to the element and ground pads 406, 407 respectively. When an electrical potential is impressed across a particular end pad 406 associated with a given element 405 and the ground pad 407, the segment (400*a* through 400*e*) associated with the particular end pad 406 is energized.

As previously described, the transducer 400 is sectioned into a small number of intertwined individual helical transducer segments (400*a* through 400*e*) that are substantially electrically insulated from one another by grooves etched through at least the outer electrode 404. This transducer design is sensitive to material defects, since any crack or imperfection could disconnect an entire segment. In addition, any discontinuous groove would short two segments. To minimize these potential problems, a suitable raw material for the transducer would include a high-density fine grain PZT ceramic material having a porosity of less then 1 mil.

When fabricating the transducer, the raw PZT ceramic material blank is originally in the form of a block or cube, and may be transformed into a tubular configuration using known machining methods. FIG. 8 is a flow diagram illustrating the method steps for making transducer 400 having a plurality of transducer segments 400*a* through 400*e* according to one embodiment of the present invention.

In one preferred embodiment, the PZT ceramic material blank is provided (step 800) and core drilled and machined using a computer numerical control machine (CNC machine) into a tubular configuration as shown in step 805. The machined tube will have an inside diameter of approximately 100 mils and an outside diameter of approximately 120 mils, providing a wall thickness of approximately 10 mils. The overall length of the PZT ceramic cylinder is also machined to approximately 325 mils. Concentricity should be under 1 mil at each end of the tube. This tubular PZT ceramic material forms what will ultimately become piezoelectric material 403. In a preferred embodiment, a quadruple YAG laser at about 700 nanometer wavelength, hooked to a rotary mandrel CAD/CAM machine is used to machine the PZT ceramic material blank into the tubular configuration.

The outer surface of the PZT cylinder 403 is then polished using methods known in the art as shown in step 810. One method acceptable to polish the PZT cylinder 403 involves mounting the cylinder 403 on a spinning mandrel and spinning the mandrel at a high speed, at which time the cylinder 403 is contacted with a very fine abrasive material, such as sandpaper or cloth. Rotational speeds of approximately 30,000 RPM or more have been found to be acceptable.

The polished finish creates a very fine, smooth surface that facilitates subsequent metallic deposition that forms the electrodes. In addition, the polished surface lessens the chance of cracks or defects in the metallic electrode surface, resulting in a very uniform and even metallic layer. The uniform metallic layer enables subsequent etching or notching of very fine grooves or patterns. In a preferred embodiment, a polished mirror finish of 10 microns or less will allow the laser etching process to yield grooves of 30 to 50 microns.

The tubular PZT ceramic material 403 is then coated with one or more metallic layers to form the inner and outer electrodes 402, 404 respectively as shown in step 815. In a preferred embodiment, the PZT ceramic material 403 is first sputtered with Gold and then Nickel-plated. The sputtering process involves placing the ceramic PZT tube 403 in a vacuum chamber, and bombarding the tube with Gold ions produced by using high temperatures and intense static electric fields between a cathode and anode.

In one embodiment of the invention the sputtering process involves placing the ceramic PZT tube 403 in a vacuum chamber outfitted with a cathode and anode. The cathode typically consists of a metal target made from the same metal to be deposited (sputtered) on the ceramic PZT tube 403. All air remaining in the vacuum chamber is evacuated, and the chamber is re-filled with a low-pressure gas, such as argon. A high voltage is impressed between the cathode and anode, ionizing the gas, and creating what is known as the Crookes dark space near the cathode. In the illustrated embodiment it is desired to sputter Gold over the PZT tube 403. Accordingly, the target is a Gold cathode. Almost all of the potential high-voltage supply appears across the dark space. The electric field accelerates the argon atoms, which bombard the Gold target. There is an exchange of momentum, and an atom is ejected from the target material (in this embodiment a Gold atom), and is deposited on the ceramic PZT tube 403, where it adheres and builds up a Gold metal film. The PZT tube 403 is rotated and flipped during the process to ensure adequate Gold coverage from all directions.

Once the gold sputtering is complete, the coated PZT tube 403 is plated using a plating process. In one preferred embodiment, coated PZT tube 403 is Nickel plated by immersing the tube 403 in a solution of Nickel and acid. Using a small electric current, the Nickel is brought out of the solution and is deposited onto the exposed surfaces of the tube.

When patterns, such as the spiral grooves forming the helical elements 405, are etched or notched into the surface of the transducer, the transducer becomes extremely fragile. To minimize transducer fatigue and failure during the machining process, the transducer assembly 400 is mounted on a mandrel prior to machining the grooves as shown in step 820. The mandrel provides additional structural support until a matching layer, described below, is place over the transducer assembly 400.

The metallic coated tube is then machined to form the inner and outer electrodes 402, 404 respectively as shown in step 825. In a preferred embodiment, the machine process to form the electrodes 402, 404 comprises laser etching the metallic coating. The combination of these materials (402, 403, 404) form transducer 400.

Both metal coating procedures are well known in the art, and may use other metals, other than Gold and Nickel in the process. In addition, the sputtering process may be eliminated when fabricating ultrasound transducers. However, the sputtering process results in stronger adherence of the metal to the ceramic PZT material, and is therefore the preferred method.

Segmentation of the transducer 400 may be accomplished by etching or notching spiral grooves into at least the outer electrode 404 of transducer 400, separating the transducer 400 into functioning discrete transducer segments (400*a* through 400*e*) as shown in step 830. The grooves can be made using several different methods known in the art, such as for example etching using a diamond wheel or laser. One particular laser machining method that may be adapted to cut helical grooves is disclosed by Corbett, Scott et al. in "Laser Machining of High Density Two-Dimensional Ultrasound Arrays" (2002), which is incorporated by reference in its entirety herein. This method uses a YAG laser emitting a wavelength of 355 nm to essentially etch or evaporate the material and create the elements 405. Other machining methods capable of achieving the desired configuration, such as those used to laser etch stents and other medical devices, may be used and are known in the art.

In a preferred embodiment a Nd-YAG laser is coupled with a CNC system accurate to within a few microns to cut the pattern. The helical grooves etched or notched by the laser are approximately 3 mils deep and 2 mils wide. The element end pads 406 and ground pad 407 as well as end grooves disconnecting the inner electrode 402 from the outer electrode 404 are similarly formed using the laser and CNC machine.

The helical elements 405 are then shorted and the transducer 400 poled in thickness mode, as shown in steps 835, 840 respectively. Shorting, or creating a "short circuit" is well known in the art with regard to ultrasonic transducer design, and involves making a temporary connection of comparatively low resistance between points in which the resistance is normally much greater. In the illustrated embodiment, a wire is used to contact and short all the transducers segments 400a through 400e (i.e. short the desired helical elements 405 and inner electrode 402).

Poling is known in the art and refers to the process of orienting the molecules of the PZT ceramic material, essentially transforming the PZT ceramic material into a piezoelectric crystal. Poling is achieved by heating the PZT ceramic material beyond its Kerrie point and applying a strong electric field. In one embodiment of the present invention, the PZT ceramic material is heated to approximately 500 degrees C. while an electric field of approximately 500 volts DC is applied. There is no need to pole each transducer segment (400a through 400e) separately. Instead, it would be sufficient to short all five segments, and apply the voltage between all five transducer elements 405a through 405e and the ground electrode 402 together.

A multi-coaxial wire is then attached to the transducer 400 as shown in step 845. In the illustrated embodiment, the multi-coaxial wire includes six (6) wires, one for each of transducer segment (400a through 400e), i.e. each of the element pads 406 and a ground lead. In a preferred embodiment, the wires are attached to the element pads 406 and ground pad 407 by soldering.

A matching layer is then placed over the transducer 400, contributing to the strength and operability of the transducer 400 assembly as shown in step 850. As previously described, the matching layer provides mechanical strength to the transducer 400 lost during the etching operation. A ceramic PZT tube with fine notches etched into the surface, as provided in a preferred embodiment of the present invention, would fracture and/or fail without an outer covering holding the material together.

The matching layer also increases the bandwidth of each transducer segment (400a through 400e), and thus the transducer's (400) overall bandwidth. As described in greater detail below, this characteristic provides a greater frequency operating range for each transducer segment 400a through 400e. To project the acoustic energy beam forward or backward relative to the transducer 400 longitudinal axis requires the transducer segments 400a through 400e to be operated out of phase from one another. Any desired change to be made to the acoustic energy beam angle is proportionally related to the frequency. Accordingly, the greater the bandwidth of the transducer segments 400a through 400e, the greater the spectrum (wider angle) the transducer 400 can project the acoustic energy beam.

The matching layer also provides electrical insulation between the transducer elements 405. In one array design, the matching layer is formed from a polymer laminated over the transducer elements 405, leaving the grooves separating the transducer elements 405 filled with air. This configuration provides acoustic separation between transducer segments 400a through 400e and insures a uniform thickness of the matching layer. However, when the transducer 400 is used for high intensity ultrasound applications, the impressed voltage between adjacent transducer segments 400a through 400e may be relatively high. This high voltage coupled with the relatively long distance the adjacent transducer elements 405 run in parallel increase the risk of current leakage between adjacent transducer segments 400a through 400e. However, the air-filled grooves provide little or no resistance to this leakage. Accordingly, in another more preferred embodiment, the transducer 400 is coated with a matching layer, preferably a low viscosity polymer, that wicks into and fills the grooves separating the transducer elements 405. The matching layer should also cover the transducer 400 with a thin polymer layer, approximately 2 mils thick. The polymers used in the matching layer should have a low viscosity, good adhesion to metal and ceramic material, low coefficient of expansion, and reasonably high dielectric strength. One example of a polymer possessing such characteristics is an epoxy adhesive.

Aside from the laminating process, the matching layer may be coated over the transducer 400 by other methods known in the art, including spray coating with an air or airless sprayer, dip coating, chemical vapor deposition, plasma coating, co-extrusion coating, spin coating and insert molding.

Figure 5A:
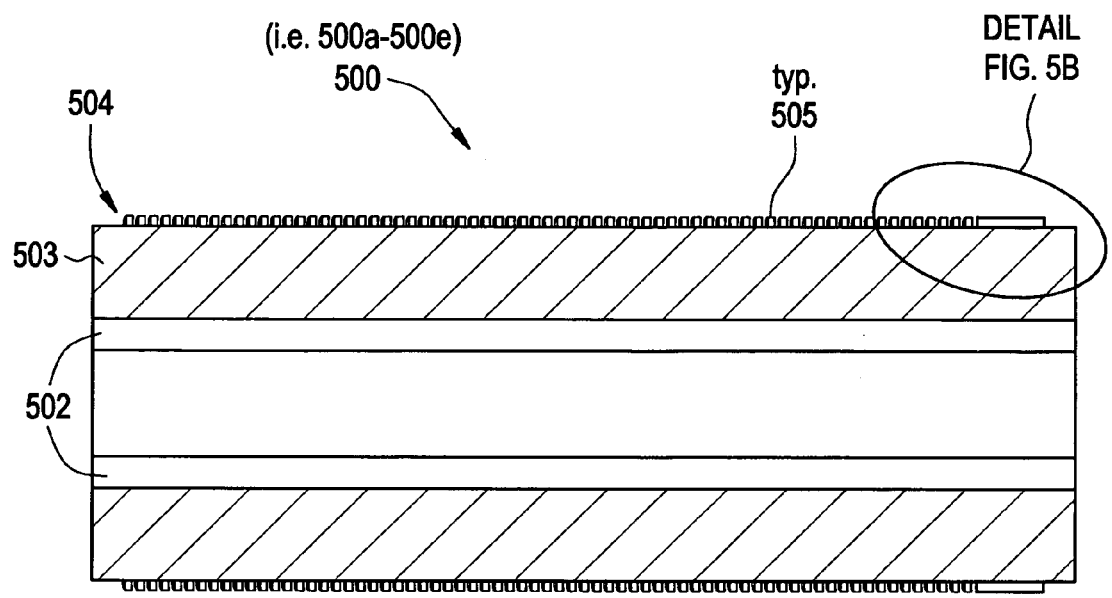
FIG. 5A is a section view showing the construction of a transducer segmented by intertwined individual helical elements essentially into an array of functionally discrete transducer segments according to one embodiment of the present invention.
Figure 5B:
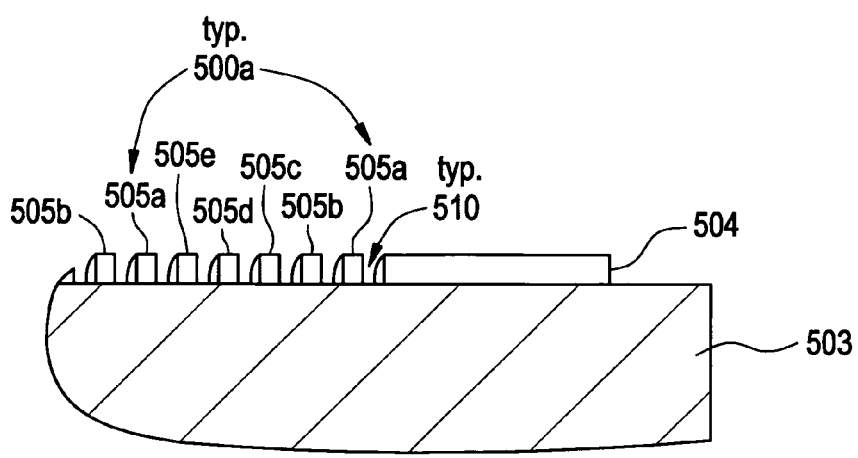
FIG. 5B is a close-up section view showing the construction of a transducer segmented by intertwined individual helical elements essentially into an array of functionally discrete transducer segments according to one embodiment of the present invention.

FIGS. 5A and 5B are section and close-up section views respectively showing the construction of a transducer 500 segmented by intertwined individual helical elements 505 (505a through 505e) essentially into an array of functionally discrete transducers segments 500a through 500e according to one embodiment of the present invention. The transducer 500 has an inner electrode 502 as a common electrode, and a cylindrical piezoelectric material 503 as a common element. The outer electrode 504 is segmented by spiral grooves 510 into 5 individual helical electrodes 505 (505a through 505e) helically arranged around the outer transducer 500 surface. The helical electrodes 505a through 505e are substantially electrically isolated from one another and correspond to the array of five helical transducers segments 500a through 500e.

When AC voltage is impressed between the inner electrode 502 and a selected one of the five outer electrode 504 elements (505a-505e), the piezoelectric material vibrates in the region between the inner electrode 502 and the selected outer electrode element 505. For example, an AC voltage impressed between the inner electrode 502 and outer electrode element 505a will cause the region between the electrode 502 and the electrode element 505a to vibrate. However, the piezoelectric material 503 is a single piece of un-sectioned material as shown in FIGS. 5A and 5B, so the impressed voltage and subsequent vibration between the inner electrode 502 and the outer electrode element 505a will cause some vibration in the regions between the inner electrode 502 and outer electrode elements 505b and 505e adjacent to electrode element 505a. This coupling of signals is sometimes referred to a cross-talk.

Figure 6A:
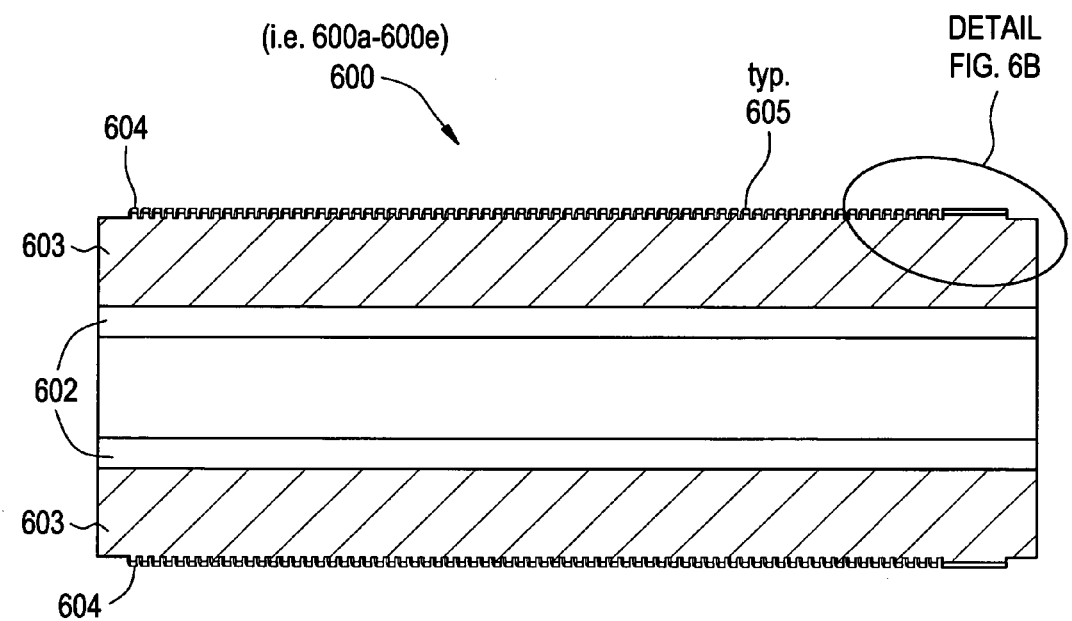
FIG. 6A is a section view showing the construction of a transducer having grooves extending through the outer electrode and into the cylindrical piezoelectric material according to one embodiment of the present invention.
Figure 6B:
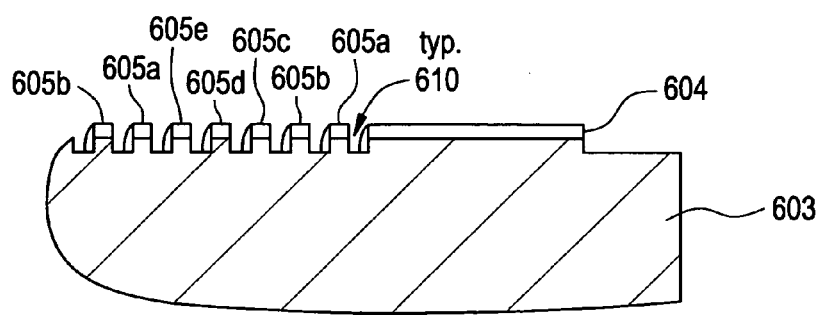
FIG. 6B is a close-up section view showing the construction of a transducer having grooves extending through the outer electrode and into the cylindrical piezoelectric material according to one embodiment of the present invention.

Excessive cross-talk between electrodes may be undesirable for some particular applications. To reduce such coupling between adjacent electrodes, the elements may be partially isolated from one another. FIGS. 6A and 6B are section and close-up section views respectively showing the construction of a transducer 600 having grooves extended into the cylindrical piezoelectric material 603 according to one embodiment of the present invention. By extending the grooves into the piezoelectric material 603, the piezoelectric material 603 will be zoned, partially isolating the signals and subsequently reducing cross-talk.

As similarly described above, transducer 600 is constructed having intertwined individual helical elements 605 sectioning transducer 600 into an array of spirally shaped functionally discrete transducer segments 600a through 600e. The transducer 600 has an inner electrode 602 as a common electrode, and a cylindrical piezoelectric material 603 at least partially as a common element. The outer electrode 604 is separated by spiral grooves 610 into 5 individual helical electrode elements 605 (605a through 605e) helically disposed around the outer transducer 600 surface. These helical elements 605a through 605e directly correspond to transducer segments 600a through 600e. However, unlike the transducer 500 illustrated in FIGS. 5A and 5B, these spiral grooves 610 radially extend completely through the outer electrode and into at least a portion of the cylindrical piezoelectric material 603. The grooves in the piezoelectric material 603 will tend to physically separate the piezoelectric material 603 into zones (five zones in the illustrated embodiment) directly corresponding to the five helical electrode elements 605a through 605e.

The coupling between the electrodes can be further reduced by extending the spiral grooves all the way through the piezoelectric material (not shown), thereby producing separate pieces of piezoelectric material, and thus completely separate transducers.

The transducers 500, 600 may be operated in at least two modes. In a first mode, all five transducer segments (simulating five helical transducers) are driven with identical signals. This mode will create a single radial acoustic energy beam having a radial thickness similar to existing single transducer designs. In a second mode, the five individual segments are driven as a standard phased array by signals having a fixed phased delay between segments. Because the segments are arranged to simulate five helical transducers, the phased array allows the resultant energy beam to be directed forward or backward.

A phased delay is a representation of the time delay in seconds experienced by each sinusoidal component of the input signal. The phase of a periodic phenomenon i.e. sinusoidal input signal, can also be expressed or specified by angular measure, with one period usually encompassing 360° (2π radians). When each transducer element is driven at the same frequency, the phase delay will be directly related to the phase shift or the change in phase angle between each sinusoidal component of the input signal.

Figure 7A:
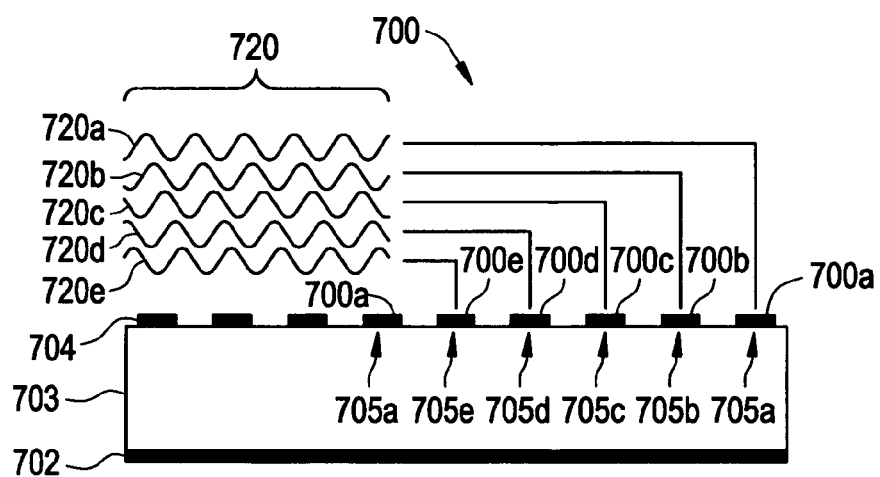
FIG. 7A is a schematic representation illustrating a fixed phase delay for sinusoidal input signals driving an array of transducers segments according to one embodiment of the present invention.

A schematic representation illustrating a fixed phase delay (phase shift) for a plurality of sinusoidal input signals 720 (720a through 720e) driving an array of transducer segments 700a through 700e is shown in FIG. 7A. This design utilizes a transducer 700 segmented into 5 intertwined helical transducer segments 700a through 700e by five helical elements 705a through 705e. The transducer segments 700a through 700e are driven through a five-channel generator with five leads. One advantage of the illustrated configuration is that it can generate a coherent phased acoustic energy beam that simulates over fifty individual elements. In the illustrated schematic, like reference numerals are used to show the association between particular fixed phase input signals 720a through 720e, transducer elements 705a through 705e, and transducer signals 700a through 700e. For example, transducer element 705a produces sinusoidal ultrasonic sound wave 720a.

When an alternating sinusoidal input current 720a through 720e is impressed between a particular element 705 of the outer electrode 704 and inner electrode 702, the thickness of the piezoelectric material 703 associated with the given transducer segment 700 (700a through 700e) will vibrate at the alternating frequency. The repetitive cyclic design illustrated in FIG. 7A produces an array that has the same signal every fifth element. Accordingly, the total cumulative phase shift over the five transducer segments 700a through 700e is equal to a full 360 degrees. Using a fixed phase delay, the optimal phase shift between adjacent transducer segments (700a through 700e) is thus 72 degrees. As can be seen from the illustrated embodiment, input signal 720a is 72 degrees out of phase from input signal 720b. Similarly, input signal 720b is 72 degree out of phase from input signal 720c, and so on. This configuration maximizes transducer efficiency and provides a coherent energy beam.

Typically, a cylindrical ultrasound transducer will produce a highly collimated acoustic energy beam that emanates from the transducer in a direction substantially normal to the transducer longitudinal axis. Similarly, a transducer having a plurality of helical segments arranged serially along a longitudinal axis would produce a highly collimated acoustic energy beam normal to the transducer longitudinal axis when the individual transducer segments are driven in-phase with respect to one another. However, when the helical segments are driven out of phase from one another, as illustrated in FIG. 7A, the resultant cumulative acoustic energy beam emanates from the transducer 700 at an angle relative to the longitudinal axis. By varying the phase delay of the input signal 720, the acoustical energy beam angle will change.

Figure 7B:
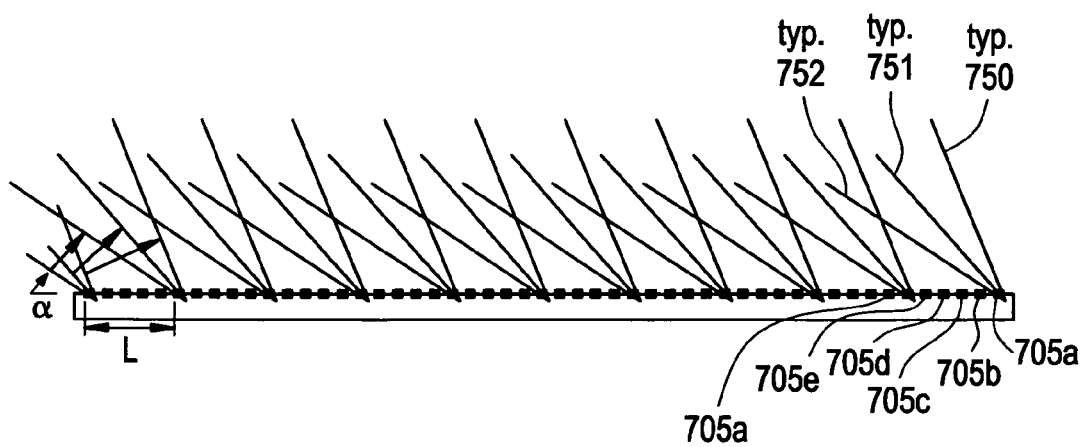
FIG. 7B is a schematic representation illustrating the resultant cumulative acoustic energy beams emanating from each of the plurality of transducer elements when driven at different frequencies according to one embodiment of the present invention.

The implication is that for a different acoustic energy beam angle, a different phase delay would be used. One method to vary the phase delay is to vary the frequency at which the transducer segments are driven while keeping the phase shift (angle) between adjacent input signals the same. FIG. 7B is a schematic representation illustrating resultant cumulative acoustic energy beams (750, 751, 752) emanating from each of the plurality of transducer element 705a when driven at different frequencies. The relationship between the angle of the acoustic energy beam and the driving frequency can be defined using the following formulas:

$$\Lambda = V/f$$

and $$\Lambda = L * \cos(\alpha)$$

Where:

Λ is the wavelength of the input signal;

V is the speed of sound in water (1550 m/sec);

f is the frequency that the transducer elements are driven;

L is the threading increment or pitch, which is defined as the linear distance traversed by the helical groove separating the transducer into helical transducer segments when making one full turn; and α is the angle between the acoustic energy beam and the longitudinal axis of the transducer.

In one preferred embodiment, the threading increment L is 0.000508 m. For the purpose of example, assume it is desired to project the acoustic energy beam at an angle 45°

(degrees) from the longitudinal axis (depicted as beam 751 in FIG. 7B). Solving the above equations simultaneously, the array of transducers 705 would have to be driven at a frequency of 4.3 MHz. In another example, assume is desired to project the acoustic the energy beam at an angle 60° from the longitudinal axis (depicted as beam 750 in FIG. 7B). Once again solving the equations simultaneously, the array of transducers 705 would have to be driven at a frequency of 6.2 MHz. Similarly, driving the transducer elements 705 at could project an acoustical energy beam 752 at an angle 30° from the longitudinal axis.

Figure 7C:
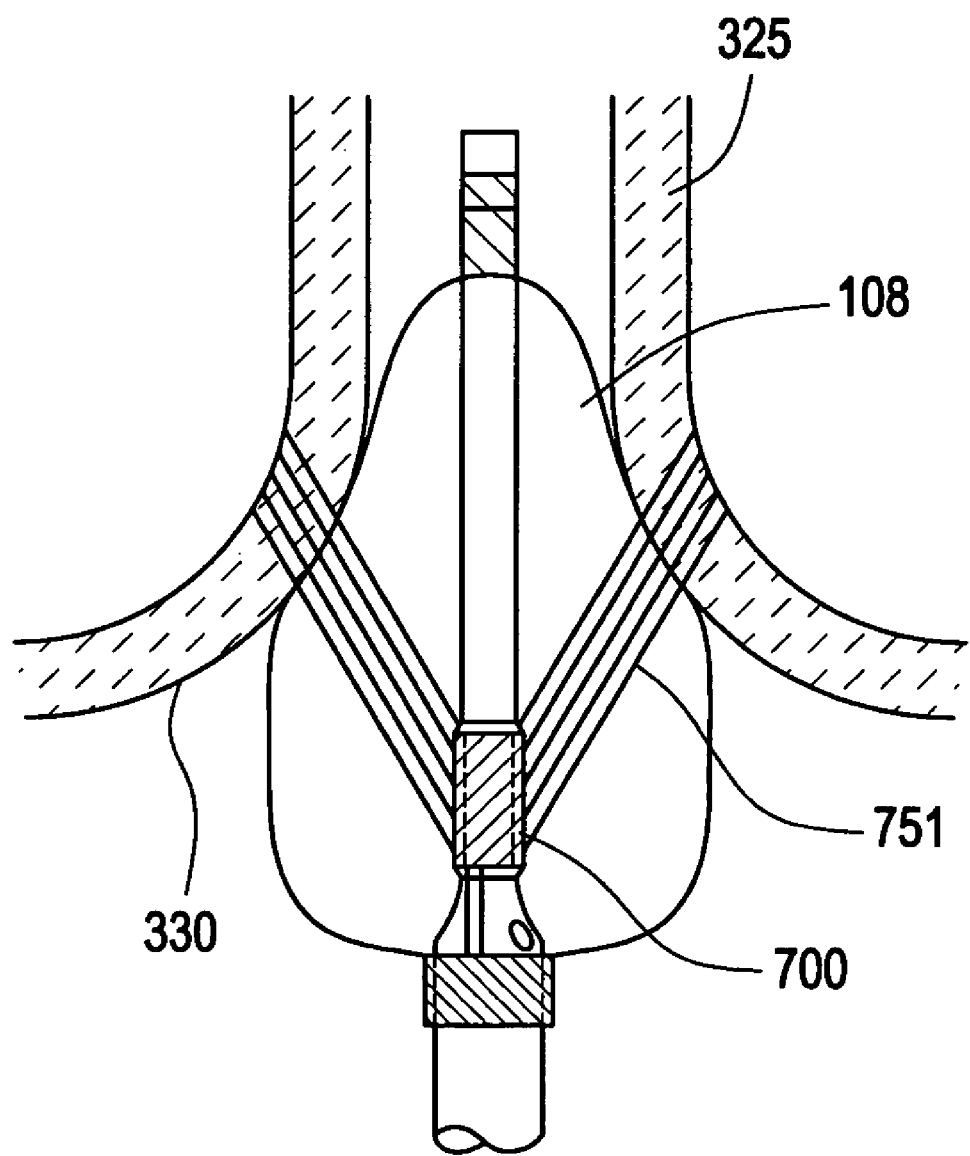
FIG. 7C is a side view of an ablation catheter showing the acoustical energy beam paths projected at an angle relative to the transducer longitudinal axis when the ablation device is placed at the juncture between a body lumen and a body cavity, such as a pulmonary vein ostium.

FIG. 7C is a side view of an ablation catheter showing the acoustical energy beam paths 751 projected at an angle relative to the transducer longitudinal axis when the ablation device is placed at the juncture between a body lumen and a body cavity, such as a pulmonary vein ostium 330.

As noted above, an acoustical energy beam can be projected at an angle 90° (i.e. perpendicular) to the longitudinal axis with any frequency in the transducer's bandwidth by driving all the elements comprising the transducer in-phase with one another. In addition, the illustrate array of transducer elements can also be driven with phase delays that are not fixed, or would not sum to 360° as previously disclosed.

Several factors should be considered when selecting a generator to produce the acoustic energy beam. The generator should have at least one channel for each electrode element (i.e. for each transducer segment). Using the illustrated embodiment as an example, the generator would be, as a minimum, a five-channel signal generator with an amplifier output stage capable of phase-lock operation. A linear RF amplifier should be provided for each channel matched for driving a 50 Ohn load up to 20 Watts per channel. The amplifiers should have a bandwidth of up to 12 MHz and should have identical gain and phase shift across the channels. The generator should preferably have directional couplers, shunt resistors to dissipate reflected power, and sensing circuits for reflected power magnitude and phase.

Preferably, the signal generator would be a computer driven signal generator capable of generating highly coherent continuous sine wave signals with accurate phase delay between the channels. The computer should be capable of obtaining the desired angle as an input, and calculate the frequency and phase for each of the five channels. Other desirable inputs to the computer should include the desirable output power, the direct and reflected power of each channel, and the target tissue temperature. If the transducer is also going to be used for imaging, appropriate considerations should be taken into the design of the generator, such as the ability to generate short bursts of acoustic energy with accurate timing.

The foregoing invention variously shows circumferential ablation device assemblies incorporating ultrasound transducers for ablating a circumferential region of tissue. Such ultrasound ablation assemblies are believed to be particularly amenable to use with the position monitoring assemblies incorporating sensing capabilities of the ablation transducer itself, such as for example but not limited to an "A"-mode sensing system. However, it is further contemplated that the particular ablation devices may also be combined with the other position monitoring assemblies and related sensors. Furthermore, such ultrasound ablation assemblies may also be combined with the various ablation monitoring assemblies, such as temperature monitoring assemblies and sensors.

As common to each of the following devices, a source of acoustic energy is provided with a delivery device that may also includes an anchoring mechanism. In one mode, the anchoring device comprises an expandable member that also positions the acoustic energy source within the body; however, other anchoring and positioning devices may also be used, such as, for example, a basket mechanism.

In a more specific form, the acoustic energy source is located within the expandable member and the expandable member is adapted to engage a circumferential path of tissue either about or along a pulmonary vein in the region of its ostium along a left atrial wall. Prior art acoustic energy sources in turn are acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, an ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of 1 millimeter to 10 millimeters. It has been observed that the ultrasonic transducer can be powered to provide a lesion having these parameters so as to form an effective conductive block between the pulmonary vein and the posterior wall of the left atrium.

While particular detailed description has been herein provided for particular embodiments and variations according to the present invention, it is further understood that various modifications and improvements may be made by one of ordinary skill according to this disclosure and without departing from the broad scope of the invention.

In addition, a circumferential ablation device assembly constructed with a mounted ultrasound ablation element according to the present invention may be used in combination with other linear ablation assemblies and methods, and various related components or steps of such assemblies or methods, respectively, in order to form a circumferential conduction block adjunctively to the formation of long linear lesions, such as in a less-invasive "maze"-type procedure.

In addition, one of ordinary skill may make other obvious or insubstantial modifications or improvements to the specific embodiments herein shown and described based upon this disclosure without departing from the scope of the invention as defined by the claims that follow.

What is claimed is:

1. A method for making a piezoelectric transducer having a plurality of intertwined indivdual helical transducer segments from comprising:

machining a ceramic material blank into a tubular configuration to form a ceramic tube;

coating the ceramic tube with a metallic layer;

machining helical grooves in the metal coated ceramic tube to form an inner electrode and a plurality of helically intertwined outer electrodes, each outer electrode having its own connection pad and electrical connection, and being associated with a functionally discrete transducer segment; and transforming the ceramic material forming the ceramic tube into a piezoelectric crystal.

2. The method of claim 1 wherein the step of machining the ceramic material blank into the tubular configuration comprises core drilling and turning the blank using a CNC machine.

3. The method of claim 2 wherein the step of core drilling and turning the ceramic material blank comprises utilizing a quadruple YAG laser at about 700 nanometer wavelength, hooked to a rotary mandrel CAD/CAM machine.

4. The method of claim 1 wherein the step of coating the tubular ceramic material with a metallic layer comprises plating the tubular ceramic material using a metal plating process.

5. The method of claim 1 wherein the step of coating the tubular ceramic material with a metallic layer comprises sputtering the ceramic tube with metal using a sputtering process.

6. The method of claim 1 wherein the step of machining helical grooves comprises laser etching the metallic coating over the ceramic tube to form inner and outer electrodes.

7. The method of claim 1 wherein the step of machining helical grooves comprises laser etching the metallic coating over the ceramic tube to form helical grooves that segment the transducer into the functionally discrete transducer segments.

8. The method of claim 1 wherein the step of transforming the ceramic material forming the ceramic tube into a piezoelectric crystal comprises shorting the transducer segments.

9. The method of claim 8 wherein the step of shorting the transducer segments comprises creating a temporary connection of comparatively low resistance between the transducer segments.

10. The method of claim 1 wherein the step of transforming the ceramic material forming the ceramic tube into a piezoelectric crystal comprises poling the ceramic tube.

11. The method of claim 10 wherein the step of poling the ceramic tube comprises:

heating the ceramic tube beyond its Kerrie point; and
apply an electric field.

12. The method of claim 1 further comprising the step of polishing the outer surface of the ceramic tube before coating the ceramic tube with a metallic layer.

13. The method of claim 12 wherein the step of polishing the outer surface of the ceramic tube comprises:
mounting the ceramic tube to a spinning mandrel;
rotating the mandrel at a high rate of speed; and
contacting the rotating ceramic tube with a fine abrasive material.

14. The method of claim 1 further comprising the step of mounting the ceramic tube to a mandrel for additional support during machining.

15. The method of claim 1 further comprising the step of applying a matching layer over the segmented transducer.

16. The method of claim 15 wherein the step of applying a matching layer comprises laminating the matching layer over the transducer.

17. The method of claim 15 wherein the step of applying a matching layer comprises coating the transducer with a polymer using a process selected from the group consisting of spray coating, dip coating, chemical vapor deposition, plasma coating, co-extrusion coating, spin coating and insert molding.

18. A method for making a piezoelectric transducer having a plurality of intertwined individual helical transducer segments comprising:
machining a ceramic material blank into a tubular configuration to form a ceramic tube;
coating the ceramic tube with a metallic layer;
machining helical grooves in the metal coated ceramic tube to form an inner electrode and a plurality of helically intertwined outer electrodes, each outer electrode being substantially electrically insulated from the immediately adjacent outer electrode; and
transforming the ceramic material forming the ceramic tube into a piezoelectric crystal.

* * * * *